(12) United States Patent
Hourani et al.

(10) Patent No.: US 12,337,271 B2
(45) Date of Patent: *Jun. 24, 2025

(54) MOBILE PURIFICATION DEVICE HAVING HEATED FILTER FOR KILLING BIOLOGICAL SPECIES, INCLUDING COVID-19

(71) Applicants: Integrated Viral Protection Solutions, LLC, Houston, TX (US); University of Houston System, Houston, TX (US)

(72) Inventors: Monzer A. Hourani, Houston, TX (US); Zhifeng Ren, Houston, TX (US); Luo Yu, Houston, TX (US)

(73) Assignees: University of Houston System, Houston, TX (US); Integrated Viral Protection Solutions, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/213,644

(22) Filed: Jun. 23, 2023

(65) Prior Publication Data

US 2023/0356133 A1 Nov. 9, 2023

Related U.S. Application Data

(63) Continuation of application No. 16/883,981, filed on May 26, 2020, now abandoned.

(Continued)

(51) Int. Cl.
| | |
|---|---|
| *B01D 39/20* | (2006.01) |
| *A61L 9/20* | (2006.01) |
| *B01D 46/00* | (2022.01) |
| *B01D 46/42* | (2006.01) |

(Continued)

(52) U.S. Cl.
CPC ............ *B01D 46/4263* (2013.01); *A61L 9/20* (2013.01); *B01D 39/2027* (2013.01);
(Continued)

(58) Field of Classification Search
CPC .............. B01D 46/4263; B01D 46/448; B01D 46/444; B01D 46/0028; B01D 46/4245;
(Continued)

(56) References Cited

U.S. PATENT DOCUMENTS

| | | |
|---|---|---|
| 2,594,101 A | 4/1952 | Volker |
| 2,849,589 A | 8/1958 | Lancaster |

(Continued)

FOREIGN PATENT DOCUMENTS

| | | |
|---|---|---|
| CN | 101929255 A | 12/2010 |
| CN | 103002606 A | 3/2013 |

(Continued)

OTHER PUBLICATIONS

Evan Nicole Brown, "This portable furnace could stop coronavirus in its tracks", Fast Company, (Mar. 18, 2020), URL: https://www.fastcompany.com/90478242/this-portable-furnace-could-stop-coronavirus-in-its-tracks, XP055869482.

(Continued)

*Primary Examiner* — Minh Chau T Pham
(74) *Attorney, Agent, or Firm* — Blank Rome LLP

(57) ABSTRACT

An apparatus used with supplied power for treating air in an environment and method of use. A housing is mobile in the environment and has an intake and an exhaust. At least one prime mover is disposed in the housing and is operable to move the air in the environment through the housing from the intake to the exhaust. At least one ultraviolet light source is disposed in the housing, is in electrical communication with the supplied power, and is configured to generate ultraviolet radiation in at least one a portion of the housing through which the moved air passes from the intake to the exhaust. At least one permeable barrier is disposed in the housing and is configured to impede the moved air flow therethrough up to an impedance threshold. The permeable (Continued)

barrier is in electrical communication to the supplied power and is heated to a surface temperature.

20 Claims, 13 Drawing Sheets

Related U.S. Application Data

(60) Provisional application No. 63/018,448, filed on Apr. 30, 2020, provisional application No. 63/018,442, filed on Apr. 30, 2020.

(51) Int. Cl.
*B01D 46/44* (2006.01)
*B60H 3/06* (2006.01)
*F24F 8/10* (2021.01)
*F24F 8/22* (2021.01)

(52) U.S. Cl.
CPC ..... *B01D 46/0028* (2013.01); *B01D 46/4245* (2013.01); *B01D 46/429* (2013.01); *B01D 46/444* (2013.01); *B01D 46/448* (2013.01); *B60H 3/0608* (2013.01); *F24F 8/10* (2021.01); *A61L 2209/11* (2013.01); *A61L 2209/111* (2013.01); *A61L 2209/12* (2013.01); *A61L 2209/14* (2013.01); *A61L 2209/15* (2013.01); *B01D 2279/50* (2013.01); *B01D 2279/65* (2013.01); *F24F 8/22* (2021.01); *F24F 2221/125* (2013.01); *F24F 2221/34* (2013.01)

(58) Field of Classification Search
CPC ............ B01D 39/2027; B01D 2279/50; B01D 2279/65; B60H 3/0608; F24F 3/1603; F24F 2003/1667; F24F 2221/34; A61L 9/20; A61L 2209/11; A61L 2209/15
USPC ..... 55/385.2, 385.1, 356, DIG. 34; 454/187; 422/121, 186.04, 186.3
See application file for complete search history.

(56) References Cited

U.S. PATENT DOCUMENTS

| | | |
|---|---|---|
| 3,395,972 A | 8/1968 | Hardison |
| 4,661,126 A | 4/1987 | Inagami |
| 4,707,167 A * | 11/1987 | Saito ............... B01D 46/523 55/385.2 |
| 5,180,409 A | 1/1993 | Fischer |
| 5,192,346 A | 3/1993 | Kowalczyk |
| 5,837,207 A | 11/1998 | Summers |
| 6,464,760 B1 | 10/2002 | Sham |
| 6,500,387 B1 | 12/2002 | Bigelow |
| 6,680,028 B1 * | 1/2004 | Harris ............... F24F 1/0071 96/132 |
| 6,716,406 B2 | 4/2004 | Reisfeld |
| 7,083,663 B2 | 8/2006 | Shih |
| 7,270,591 B2 | 9/2007 | Deshpande |
| 7,625,277 B2 * | 12/2009 | Palmer ............... A61L 9/20 454/238 |
| 8,263,012 B2 | 9/2012 | Hay |
| 8,444,747 B2 * | 5/2013 | Kristensson ......... F24F 5/0042 128/202.13 |
| 8,529,830 B2 | 9/2013 | Zhou |
| 8,772,744 B1 | 7/2014 | Liu |
| 10,117,961 B2 | 11/2018 | Horne |
| 10,471,170 B2 | 11/2019 | Lee |
| 11,446,600 B2 | 9/2022 | Hourani |
| 2004/0003581 A1 | 1/2004 | Lim |
| 2004/0041564 A1 | 3/2004 | Brown |
| 2004/0047776 A1 | 3/2004 | Thomsen |
| 2005/0092181 A1 * | 5/2005 | Shih ............... H05B 3/12 55/490.1 |
| 2008/0031783 A1 | 2/2008 | Briggs |
| 2008/0086994 A1 | 4/2008 | Descotes |
| 2008/0121823 A1 | 5/2008 | Goel |
| 2010/0032055 A1 | 2/2010 | Sangi |
| 2010/0323603 A1 | 12/2010 | Lans |
| 2011/0308522 A1 | 12/2011 | Kimm |
| 2012/0192717 A1 | 8/2012 | Gonze |
| 2012/0196147 A1 | 8/2012 | Rabiei |
| 2013/0256631 A1 | 10/2013 | Khan |
| 2013/0294968 A1 | 11/2013 | Owen |
| 2014/0369894 A1 | 12/2014 | Hingorani |
| 2015/0092181 A1 | 4/2015 | Nishita |
| 2015/0359921 A1 | 12/2015 | Palmer |
| 2016/0067647 A1 | 3/2016 | Tate |
| 2017/0028820 A1 | 2/2017 | Walsh |
| 2017/0139386 A1 | 5/2017 | Pillai |
| 2017/0292797 A1 | 10/2017 | Roberge |
| 2018/0050124 A1 | 2/2018 | Lee |
| 2019/0063763 A1 | 2/2019 | Kleinberger |
| 2019/0083673 A1 | 3/2019 | Munn |
| 2020/0009286 A1 | 1/2020 | Zarcone |
| 2020/0086257 A1 | 3/2020 | Liu |
| 2020/0182496 A1 | 6/2020 | Xiao |
| 2020/0300460 A1 | 9/2020 | Rush, III |
| 2021/0339183 A1 | 11/2021 | Hourani |
| 2021/0339184 A1 | 11/2021 | Hourani |
| 2023/0119976 A1 | 4/2023 | Maletich |

FOREIGN PATENT DOCUMENTS

| | | |
|---|---|---|
| CN | 203731560 U | 7/2014 |
| CN | 204404388 U | 6/2015 |
| CN | 204478279 U | 7/2015 |
| CN | 205593084 U | 9/2016 |
| CN | 206919206 U | 1/2018 |
| CN | 206973703 U | 2/2018 |
| CN | 206973773 U | 2/2018 |
| CN | 108779925 A | 11/2018 |
| CN | 108981014 A | 12/2018 |
| CN | 209524549 U | 10/2019 |
| CN | 111043670 A | 4/2020 |
| CN | 112325461 A | 2/2021 |
| JP | S47044891 | 11/1972 |
| JP | S50128324 | 10/1975 |
| JP | S50128324 U | 10/1975 |
| JP | S60193517 | 10/1985 |
| JP | S61171514 A | 8/1986 |
| JP | H01210010 A | 8/1989 |
| JP | H09126551 A | 5/1997 |
| JP | 2004508163 A | 3/2004 |
| JP | 2004130173 A | 4/2004 |
| JP | 2005013687 A | 1/2005 |
| JP | 2005137871 A | 6/2005 |
| JP | 2007044432 A | 2/2007 |
| JP | 2011224121 A | 11/2011 |
| JP | 2015104400 A | 6/2015 |
| JP | 6019351 | 11/2016 |
| JP | 2018509499 A | 4/2018 |
| KR | 20100036438 A | 4/2010 |
| KR | 20170035481 A | 3/2017 |
| KR | 20180003833 A | 1/2018 |
| WO | 0220064 A2 | 3/2002 |
| WO | 2004006969 | 1/2004 |
| WO | 2005075000 A1 | 8/2005 |
| WO | 2005124241 A1 | 12/2005 |
| WO | 2016135257 A2 | 9/2016 |
| WO | 2019056323 A1 | 3/2019 |
| WO | 2019204570 A1 | 10/2019 |
| WO | 2021221698 A1 | 11/2021 |
| WO | 2021221699 A1 | 11/2021 |

OTHER PUBLICATIONS

Extended European Search Report issued Dec. 6, 2023 in counterpart European Patent Application No. 20933580.1 (10 pages).

(56) References Cited

OTHER PUBLICATIONS

Final Office Action in U.S. Appl. No. 17/118,379, mailed Jul. 20, 2021, 9-pgs.
First Examination Report in counterpart GCC Appl. 2020-40143, dated Aug. 31, 2021,4-pgs.
First Examination Report in counterpart GCC Appl. 2020-40144, dated Aug. 31, 2021,4-pgs.
First Office Action in counterpart Chinese Appl. 202010849059.3, dated Jul. 29, 2021, 6-pgs.
First Office Action in counterpart Chinese Appl. 202010849987.X, dated Jul. 29, 2021, 6-pgs.
First Office Action in counterpart Japanese Appl. 2020-129200, mailed Jun. 8, 2021.
First Office Action in counterpart Japanese Appl. 2020-129203, mailed May 11, 2021.
High-Performance Alloys for Resistance to Aqueous Corrosion, 2001, obtained from URL at https://www.parrinst.com/wpcontent/uploads/downloads/2011/07/Parr_Inconel-Incoloy-Monel-Nickel-Corrosion-Info.pdf.
International Search Report and Written Opinion Corresponding to Application No. PCT/US2021/062204, mailed Jan. 11, 2022.
International Search Report and Written Opinion in PCT Appl. PCT/US20/35608, mailed Oct. 20, 2020.
International Search Report and Written Opinion in PCT Appln PCT/US20/35607, mailed Sep. 8, 2020.
International Search Report mailed Sep. 8, 2020 issued in counterpart PCT Application No. PCT/US2020/035607.
Notice of Reasons for Refusal in counterpart JP Appl. 2020-129203, dated Jan. 11, 2022,11-pgs.
Office Action in U.S. Appl. No. 17/118,379, mailed Apr. 7, 2021, 8-pgs.
Office Action issued Feb. 26, 2024 in corresponding U.S. Appl. No. 18/213,644 (10 pages).
Office Action issued Mar. 28, 2024 in corresponding U.S. Appl. No. 17/889,596 (11 pages).
Search Report and Written Opinion in counterpart Singapore Appl. 10202007442S, dated Sep. 10, 2021,11-pgs.
Search Report and Written Opinion in counterpart Singapore Appl. 10202007444V, dated Jan. 20, 2022,10-pgs.
Second Notice of Reasons for Refusal in counterpart JP Appl. 2020-129200 dated Mar. 8, 2022, 7 pages.
Second Notice of Reasons for Refusal in counterpart JP Appl. 2020-129203, dated Jan. 11, 2022, 11-pgs.
Yu, L. et al., "Catching and killing of airborne SARS-CoV-2 to control spread of COVID-19 by a heated air disinfection system," Materials Today Physics, 15 (2020) 100249, Jul. 7, 2020, 5-pgs.
Office Action issued Sep. 26, 2024 in counterpart Mexican Application No. MX/a/2020/009035. 6 pages.
Decision to Grant issued Mar. 5, 2025 in counterpart Japanese Application No. 2022-566444 (with translation). 6 pages.
Decision to Grant issued Mar. 5, 2025 in counterpart Japanese Application No. 2022-566443 (with translation). 6 pages.

* cited by examiner

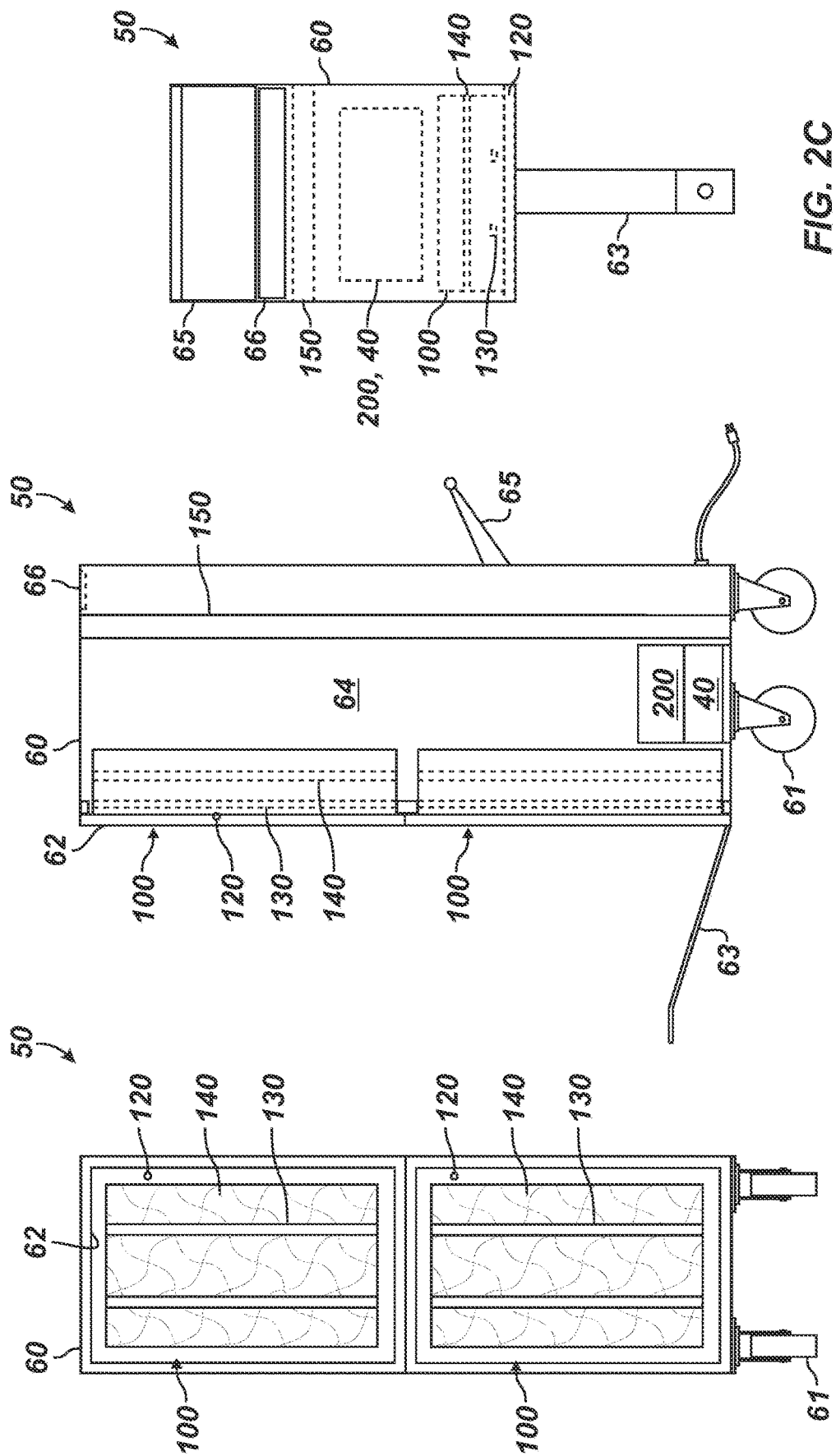

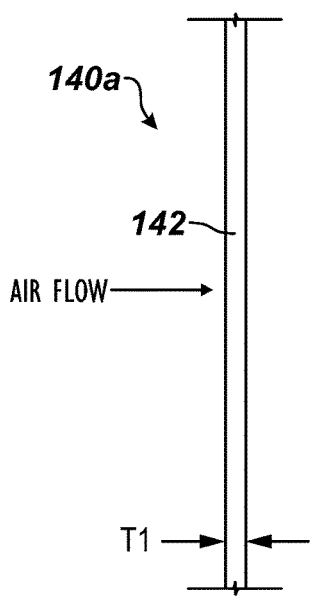
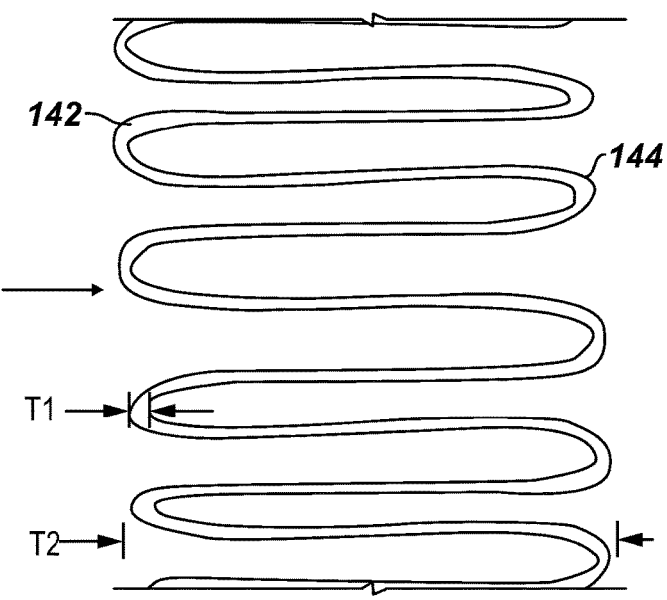
FIG. 9A
FIG. 9B
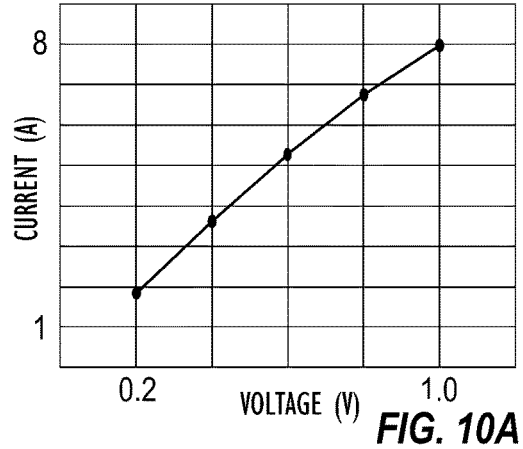
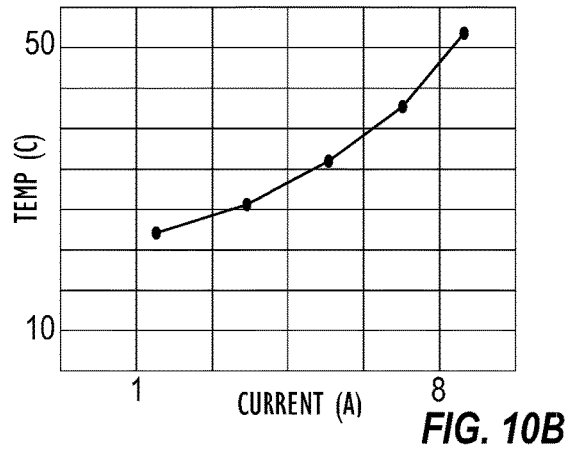
FIG. 10A
FIG. 10B
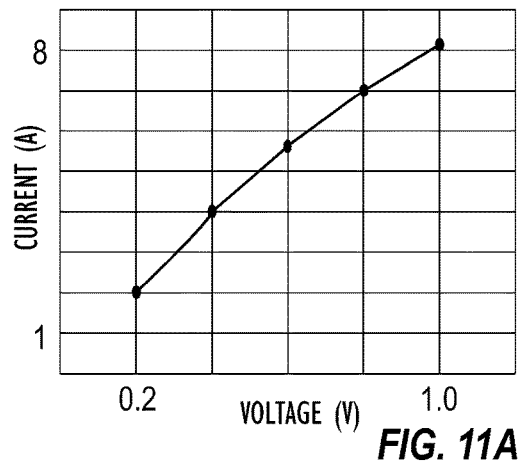
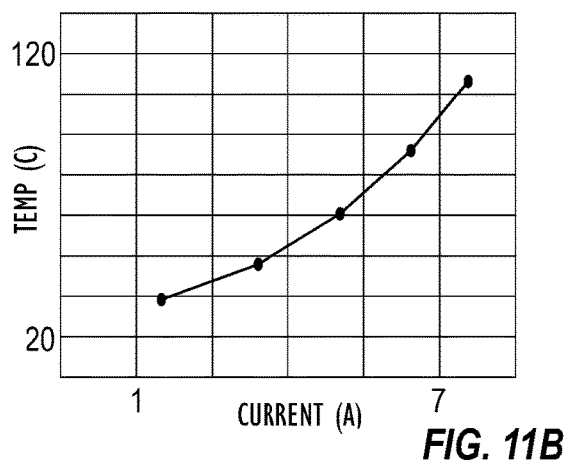
FIG. 11A
FIG. 11B

MOBILE PURIFICATION DEVICE HAVING HEATED FILTER FOR KILLING BIOLOGICAL SPECIES, INCLUDING COVID-19

CROSS-REFERENCE TO RELATED APPLICATIONS

This application is a continuation of U.S. application. Ser. No. 16/883,981, filed May 26, 2020, which claims priority to U.S. Provisional Application. Nos. 63/018,442 and 63/018,448, both filed Apr. 30, 2020, the subject matter of each of which is incorporated herein by reference.

This application may also relate to co-pending U.S. Application No. 16,883,977, filed on May 26, 2020 and entitled Purification Device Having Heated Filter for Killing Biological Species, Including COVID-19, the subject matter of which is incorporated herein by reference.

BACKGROUND OF THE DISCLOSURE

Various infectious pathogens, including bacterium, viruses, and other microorganism can cause disease in humans. The deadly Human SARS-COV-2 strain (COVID-19) pandemic has impacted the human condition at all levels of life around the globe. The COVID-19 infection is persistently spread by circulating air flow as the primary mechanism for transmission. There are few active strategies to protect the public against COVID-19, and currently strategies are widely debated, costly, and inefficient. A passive approach to condition and purify circulating air in all environments is needed to combat aerosolized COVID-19 immediately because current filter and air-purification technologies are not successful at killing the small sized (0.05-0.2 microns) COVID-19 virus.

Overall, air filtration is used in heating, ventilating, and air conditioning (HVAC) systems to remove dust, pollen, mold, particulates, and the like from the air being moved through a facility by the system. The filters used for the filtration can come in a number of forms and can be configured to filter particles of a given size with a given efficiency.

For example, high-efficiency particulate air (HEPA) filters are commonly used in cleanrooms, operating rooms, pharmacies, homes, etc. These filters can be made of different types of media, such as fiberglass media, ePTFE media, etc., and may have activated carbon-based material. In general, HEPA filters can filter over 99 percent of particles with a diameter of a given size (e.g., 0.3 microns or larger in size). Even with their efficiency, HEPA filters may not stop pathogens (virions, bacteria, etc.) of very small size.

Ultraviolet (UV) germicidal lights can stop pathogens, such as bacteria, viruses, and mold. The UV germicidal lights produce ultraviolet radiation, which can then damage the genetic material of the microorganisms. The damage may kill the pathogen or make them unable to reproduce. Extended exposure to the UV radiation can also break down pathogens that have deposited on an irradiated surface.

One example of an ultraviolet system includes an upper room air ultraviolet germicidal irradiation (UVGI) system. In the UVGI system, the UV germicidal light is installed near the ceiling in an occupied room. Air circulated by convection near the ceiling in the upper portion of the space is then irradiated within an active field of the UV germicidal light. UVGI systems can also be installed in the ducts of HVAC systems and can irradiate the small airborne particles containing microorganisms as the air flows through the ducts.

Although existing systems for filtration and germicidal irradiation can be effective in treating air to remove particulates and damage pathogens, there is a continuing need to purify air in populated environs, such as facilities, homes, workspaces, hospitals, nursing homes, sporting venues, and the like, to reduce the spread of pathogens, such as bacteria, viruses, and molds, even more.

In particular, the 2019 novel coronavirus disease (COVID-19) is a new virus of global health significance caused by infection of severe acute respiratory syndrome coronavirus 2 (SARS-COV-2). COVID-19 is thought to spread from person to person in close contact through respiratory droplets. Studies show the virus can survive for hours at a time and can be persistently carried by airflow. For this reason, it is believed that a stationary 6-feet separation is ineffective in a situation where people spend a long time together in a room because infection can simply be carried by the airflow.

For example, COVID-19 (Sars-COV-2) may survive in droplets for up to three hours after being coughed in the air, and convection in the air is thought to be the primary mechanism for the spread of the infection. Accordingly, droplet-spray and convection can drive direct airborne infection, and social distancing can be ineffective for enclosed environments were people spend a long time together.

As there is no current cure for COVID-19, environmental purification strategies can help slow the spread of the virus. Unfortunately, current systems to treat circulated air are expensive and use primarily UV germicidal light. These products require professional installation, are not accessible to the general public per se, and have not been used to kill COVID-19. Moreover, filtration in an HVAC system can be ineffective. COVID-19 measures between 0.05 to 0.2 microns, but HEPA filters can filter particulate larger than 0.3 microns so additional protection is needed against the spread of COVID-19.

For these reasons, the subject matter of the present disclosure is directed to overcoming, or at least reducing the effects of, one or more of the problems set forth above.

SUMMARY OF THE DISCLOSURE

The subject matter of the present disclosure is directed to a mobile purification device that filters air and seeks to destroy pathogens (viruses, bacteria, mold, pollens, etc.) and other elements, such as volatile organic compounds, allergens, and pollutants. The purification device is configured to be affordable, easily installed, accessible and useable in both residential and commercial settings. The purification device can be applied to real world solutions to best reduce viruses, such as COVID-19, and other pathogens in the circulating air, and the purification device can be deployed as a specialized heated filter for use in commercial, residential, mass transit, and public venues, for example.

For example and as discussed below, the purification device includes a barrier heater or heated filter that uses targeted thermal conduction of high efficiency nickel foam/mesh raised to temperatures proven to kill pathogens, such as corona viruses (such as COVID-19). The purification device can also include an ultraviolet (UV) light sources that uses UV-C light to destroy the virus. The UV light source and the barrier heater are combined together in a flame retardant and resistant filtration system, which can then be moved and placed as desired in an environment of a facility or populated environs, such as an airport terminal, church, hospital, workshop, office space, residence, transit vehicle, school, hotel, cruise ship, recreational venue, etc. As there is no current cure for COVID-19 and many other pathogens, environmental purification strategies can help slow the spread of the virus, and the air purification provided by the disclose device can provide a primary defense against transmission.

According to one configuration, an apparatus is used with supplied power for treating air in an environment. The apparatus comprises a housing, at least one prime mover, at least one ultraviolet light source, at least one heater.

The housing is mobile in the environment. The housing may also be robotic, having powered wheels for moving in the environment. The housing has an intake and an exhaust. The at least one prime mover disposed in the housing between the intake and the exhaust is operable to move the air in the environment through the housing from the intake to the exhaust. The at least one UV light source disposed in the housing is connected in electrical communication with the supplied power and is configured to generate an active field of ultraviolet radiation in at least one a portion of the housing through which the moved air passes from the intake to the exhaust. The at least one heater is disposed across a surface area of the housing and comprises a permeable barrier of metal material. The permeable is configured to impede the moved air flow therethrough up to an impedance threshold, and the permeable barrier connected in electrical communication to the supplied power is heated to a surface temperature.

In another configuration, a method is used for treating air in an environment. Air flow is moved through a plenum in a mobile housing from an intake to an exhaust by powering a prime mover disposed in the plenum. The air flow is filtered up to a filtration threshold through a filter disposed across a surface area of the plenum. An active field of ultraviolet radiation is produced in the housing by powering an ultraviolet light source disposed in the plenum. Meanwhile, the air flow is impeded up to an impedance threshold through a permeable barrier of a heater disposed across the surface area of the plenum and having a metal material. The permeable barrier is heated to a surface temperature by supplying a voltage potential across the permeable barrier.

This summary is not intended to identify essential features of the claimed subject matter, nor is it intended for use in determining the scope of the claimed subject matter. It is to be understood that both the foregoing general description and the following detailed description are exemplary and are intended to provide an overview or framework to understand the nature and character of the disclosure.

BRIEF DESCRIPTION OF THE DRAWINGS

The accompanying drawings are incorporated in and constitute a part of this specification. It is to be understood that the drawings illustrate only some examples of the disclosure and other examples or combinations of various examples that are not specifically illustrated in the figures may still fall within the scope of this disclosure. Examples will now be described with additional detail through the use of the drawings, in which:

FIGS. 2A, 2B, and 2C illustrate front, side, and top views of a mobile purification device according to the present disclosure.

FIGS. 9A and 9B illustrates side views of the permeable barrier for the disclosed heater in flat and corrugated configurations.

FIGS. 10A and 10B illustrate graphs for the barrier heater having a flat configuration.

FIGS. 11A and 11B illustrate graphs for the barrier heater having a corrugated configuration.

DETAILED DESCRIPTION OF THE DISCLOSURE

The subject matter of the present disclosure is directed to a purification device for instantaneously eradicating pathogens, such as COVID-19 virus, from the circulating air by filtering and exposing the pathogens to high temperatures (above 200° C.) (above 392° F.). By doing so, the subject matter of the present disclosure can decrease infectious transmission of a virus and other biological species that may cause future pandemics, while providing a sense of security and peace of mind for the public to return to work, school, life, recreation and healthcare in a post-COVID-19 world.

The primary mechanism of action of the purification device is a specialized heated filter or barrier heater that uses a low energy, targeted thermal conduction of high performance, high resistant porous metal foam incased in a flame retardant frame. The disclosed heated filter or barrier heater can be combined with a highly-efficient HVAC filter. Additionally, ultraviolet light (UV-C) can be added to the system milieu for additive killing effect. Research has shown heat and low wavelength light can successfully deactivate COVID-19 with duration of exposure.

As disclosed below, the mobile/robotic COVID-19 purification device can be deployed for use in public venues, healthcare facilities, nursing homes, schools, airplanes, trains, cruise ships, performance venues, theaters, churches, grocery and retail stores, prisons, etc. Using the same technology, the purification device of the present disclosure can be incorporated into air handling systems of a facility, vehicle, or any other environment. Further details are provided in the related co-pending U.S. application Ser. No. 16/883,977, entitled "Purification Device Having Heated Filter for Killing Biological Species, Including COVID-19", which is incorporated herein by reference in its entirety.

Figure 1:
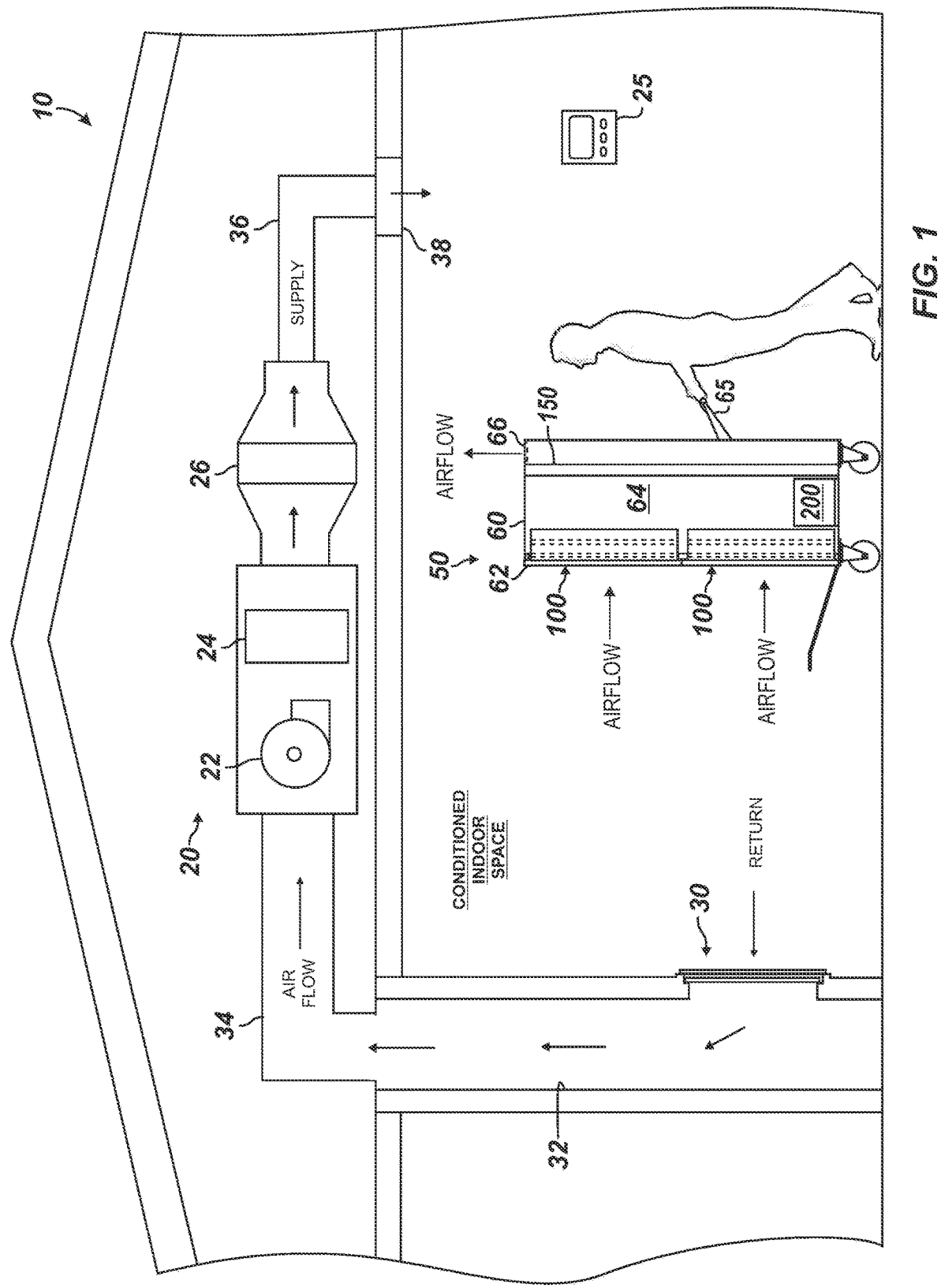
FIG. 1 illustrates an environment having a mobile purification device according to the present disclosure.

As shown in FIG. 1, a facility environment 10, such as a home, hospital, office space, airport terminal, church, or other enclosed environment, has an air handling system 20, such as a heating, ventilating, and air conditioning (HVAC) system, although other air handling systems can be used. As is typical, the HVAC system 20 includes returns 30, chases 32, return ducts 34, etc. that direct drawn return air from an indoor space to a blower 22, heat exchanger 24, and coiling coil 26 of the system 20. In turn, the system 20 provides conditioned supply air to the space through supply ducts 36, vents 38, and the like. The heat exchanger 24 can include an electric or gas furnace for heating the air. The cooling coil 26 can be an evaporator connected in a cooling circuit to other conventional components outside the facility, such as a condenser, compressor, expansion valve, etc.

One or more mobile purification devices 50 are used in the facility environment to purify the air. As shown here, the mobile purification device 100 can be used in a space of a facility environment. Several spaces in the facility environment may have such a mobile purification device 100.

Briefly, the mobile purification device 50 includes a housing 60 that is mobile in the environment and that has an intake 62 and an exhaust 66. The device 50 has one or more purification elements or cartridges 100 and a prime mover 150. The purification elements 100 disposed toward the intake 62 can include at least one or more ultraviolet light sources and one or more permeable barriers. The device 50 can also include one or more filters at the intake 62. For mobility, the mobile housing 60 can have caster wheels 61, a tow hitch 63, and a handle 65.

Study of airflow in a meeting room and office space shows that convection patterns can persistently carry infection between chairs at a conference table and between cubicles in an open office space. This shows that reliance on separation between people can be ineffective due to the convention of the air in a populated environment.

Control of the mobile purification device 50 can be handled entirely by a local controller 200, which determines independently the device's operation. Alternatively, the local controller 200 can be integrated with a system controller 25 for the HVAC system 20, which can signal activation of the system 20. In a further alternative, the mobile purification device 50 may lack local controls and may be centrally controlled by the system controller 25. As will be appreciated, these control arrangements can be used in any combination throughout a facility 10, multiple purifications devices 100, conditioning zones, and the like.

FIGS. 2A, 2B, and 2C illustrates front, side, and top view of a mobile purification device 50 according to the present disclosure for treating air in an environment. As discussed above, the apparatus 50 includes the housing 60 having the prime mover 150. The apparatus 50 includes one or more permeable barrier heaters 140 and can include one or more UV light sources 130. As noted above, the barrier heaters 140 can be housed in one or more elements or cartridges 100 installed in the device's housing 60. The UV light sources 130 may also be housed in the cartridges 100. Filters 120 for positioning at the intake 62 are labelled, but not shown.

As shown, the intake 62 can be an open side of the housing 60 for intaking environmental air across a larger surface area, while the exhaust 66 can be a port out of the top of the housing 60 directing treated air in an upper area of the environment. The housing 60 has sidewalls enclosing an interior or main plenum 64 for passage of air flow therethrough from the intake 62 to the exhaust 66. The at least one prime mover 150 is disposed in the housing 60 between the intake 62 and the exhaust 66 and is operable to draw in the air from the environment through the intake 62 and exhaust treated air back to the environment through the exhaust 66.

As noted generally herein, the apparatus 50 can include at least one filter 120 disposed in the housing 60, such as being disposed at the intake 62. The at least one filter 120 is configured to filter the moved air therethrough up to a filtration threshold, the one or more barrier heaters 140 are disposed in the housing 60 to impede the moved air flow therethrough up to an impedance threshold. The one or more barrier heaters 140 are connected in electrical communication to the supplied power and are heated to a target surface temperature.

If used, the one or more UV light sources 130 disposed in the housing 60 are connected in electrical communication with supplied power and are configured to generate ultraviolet radiation in at least a portion of the housing 60 through which the moved air passes from the intake 62 to the exhaust 66.

As particularly shown in FIGS. 2A-2C, the apparatus 50 has at least one purification element or cartridge 100 configured to replaceably position at the intake 62 of the housing 60. (Two cartridges 100 are shown in the Figures.) The cartridge 100 has a plenum between an inlet and an outlet, and the UV light source 130 and the permeable barrier heater 140 are housed in the cartridge 100. The cartridge 100 can include a dedicated filter 120 at the inlet so that multiple filters 120 on multiple cartridges 100 can cover the intake 62 of the apparatus' housing 60. As an alternative, the housing 60 may have a unitary filter (not shown) that covers the intake 62 separately from the cartridges 100.

As will be appreciated with the benefit of the present disclosure, use of the cartridges 100 is not strictly necessary, as the plenum 64 of the housing 60 can include one or more UV light sources 130 and barrier heaters 140 mounted and maintained therein. However, use of the cartridges 100 makes the purification device 50 more modular, facilitating maintenance and replacement. For example, the cartridges 100 may be removable and replaceable components in the housing 60 so the purification device 50 can be configured for a given implementation with different elements and so operational components can be replaced. Although the one or more cartridges 100 are shown as being arranged across the surface area of the intake 62 of the housing, other configurations can be used. For example, cartridges 100 may be arranged in series to serially treat air flow, as well as being arranged in parallel.

To treat air in the environment, air flow is moved through the main plenum 64 in the mobile housing 60 from the intake 62 to the exhaust 66 by powering the prime mover 150 disposed in the plenum 64. As shown, the prime mover 150 can be disposed downstream of the filters 120, UV light sources 130, and the barrier heaters 140 so that air is drawn through the apparatus 50, which is suitable for filtration purposes. In general, the prime mover 150 comprises one or more blowers, fans, etc. For example, multiple fans of the prime mover 150 can be used to cover the surface area inside the housing 60.

Power can be supplied to the mobile purification device 50 from available power sources in the environment, such as a conventional AC outlet. As shown here, the apparatus 50 can include a power cord for connecting to facility power. The apparatus 50 can include its own power supply 40 disposed on the housing to provide the supplied power. For instance, a rechargeable battery can be used for the power supply 40.

The air flow is filtered up to a filtration threshold through the one or more filters 120 disposed in the plenum 64 (i.e., disposed at the intake 62 or disposed across the intake 62 or portion thereof). Ultraviolet radiation is produced in the housing 60 by powering the UV light sources 130 disposed in the plenum 64. Furthermore, the air flow is impeded up to an impedance threshold through the one or more barrier heaters 140 disposed in the plenum 64. The barrier heaters 140 are heated to a surface temperature by supplying a voltage potential across them. The drawn air is then passed out the exhaust 66 toward the top of the housing 60 so that any heated flow and any recently treated air is exhausted in the environment away from surrounding people and objects.

The mobile purification device 50 also includes a controller 200 disposed in electrical communication with the UV light source(s) 130, the barrier heaters 140, and the prime mover 150. As described in more detail below, the controller 200 is configured to control (i) the radiation of the UV light source(s) 130 powered by the supplied power, (ii) the heating of the barrier heater(s) 140 powered by the supplied power, and (iii) the air flow drawn by the prime mover 150 through the housing 60 from the intake 62 to the exhaust 68.

Figure 3C:
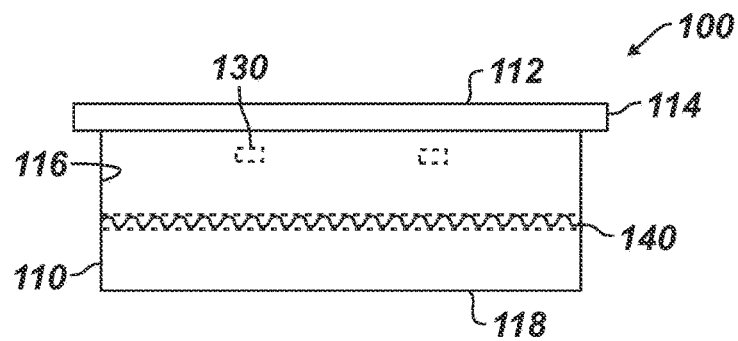
FIGS. 3A, 3B, and 3C illustrate front, side, and end views of a purification cartridge for the purification device of the present disclosure.
Figure 3A:
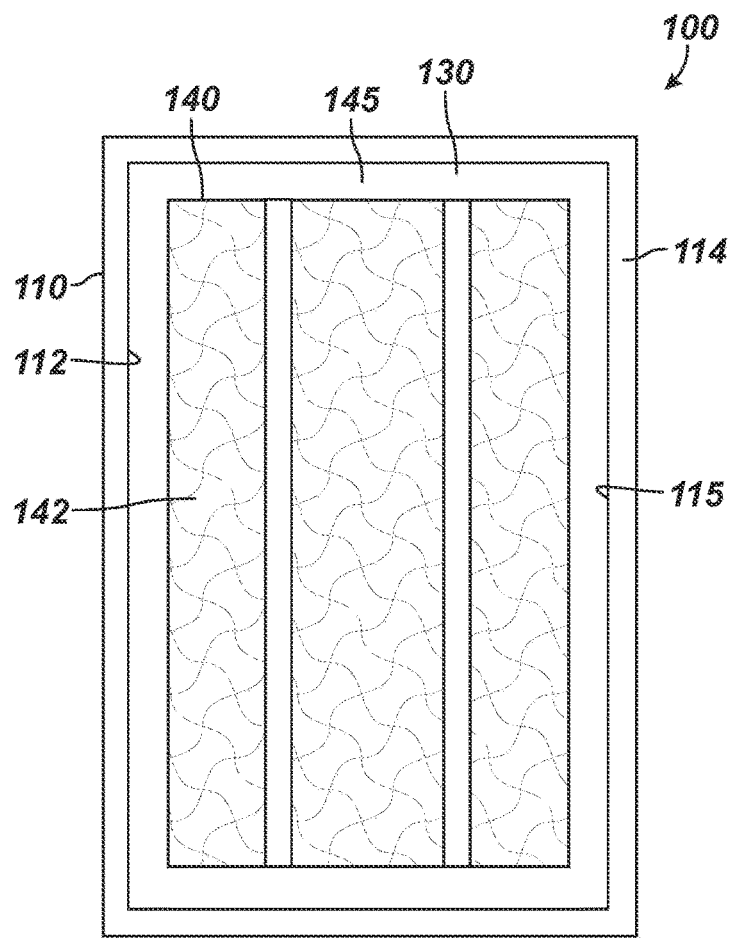
Figure 3B:
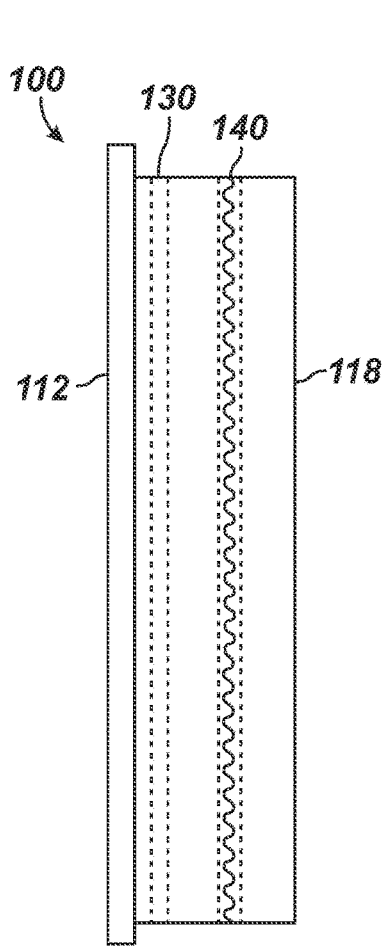

With an understanding of how the mobile purification device 50 is used and where it can be installed in a facility, discussion now turns to particular details of the disclosed purification device 50. As noted above, the mobile purification device 50 can use one or more cartridges 100 that integrate together filters 120, UV light sources 130, and barrier heaters 140. For example, FIGS. 3A, 3B, and 3C illustrate front, side, and end views of an example purification cartridge 100 of the present disclosure. The cartridge 100 includes a frame 110 configured for installation in the intake (62) of the mobile device's housing (60).

Overall, the frame 110 has four sidewalls enclosing a plenum inside 116, which is exposed on opposing open faces (one for an inlet 112 and another for an outlet 118 of the plenum 116). If necessary, the inlet 112 can include a rim 114, which would typically engage around the opening for the intake (62: FIGS. 2A-2C). Fasteners (not shown) can affix the rim to surrounding structures. Although configured for a particular implementation, a typical size for the frame 110 may include overall dimensions of 20-in width×30-in height×7-in depth.

As best shown in FIG. 3A, the inlet 112 or the rim 114 may form a receptacle for holding a filter (not shown) to filter entering air flow into the frame's plenum 116. Inside the plenum 116, the frame 110 holds a barrier heater 140. As briefly shown here, the barrier heater 140 includes a permeable barrier 142, composed of metal and comprising a mesh, a foam, a screen, or a tortuous media, supported by a surrounding case 145 and disposed across the plenum 116 to provide a permeable surface area for treating the air flow as discussed below.

Also inside the plenum 116, the frame can hold an UV light source 130 as an additional treatment in conjunction with the barrier heater 140. (Other embodiments disclosed herein may not include the UV light source 130.) As briefly shown here, the UV light source 130 includes two UV-C light emitting diode (LED) strips placed across the plenum 116 to provide an active field for treating the air flow as discussed below. More or fewer sources 130 can be used, and different types of sources 130 can be installed.

Figure 4A:
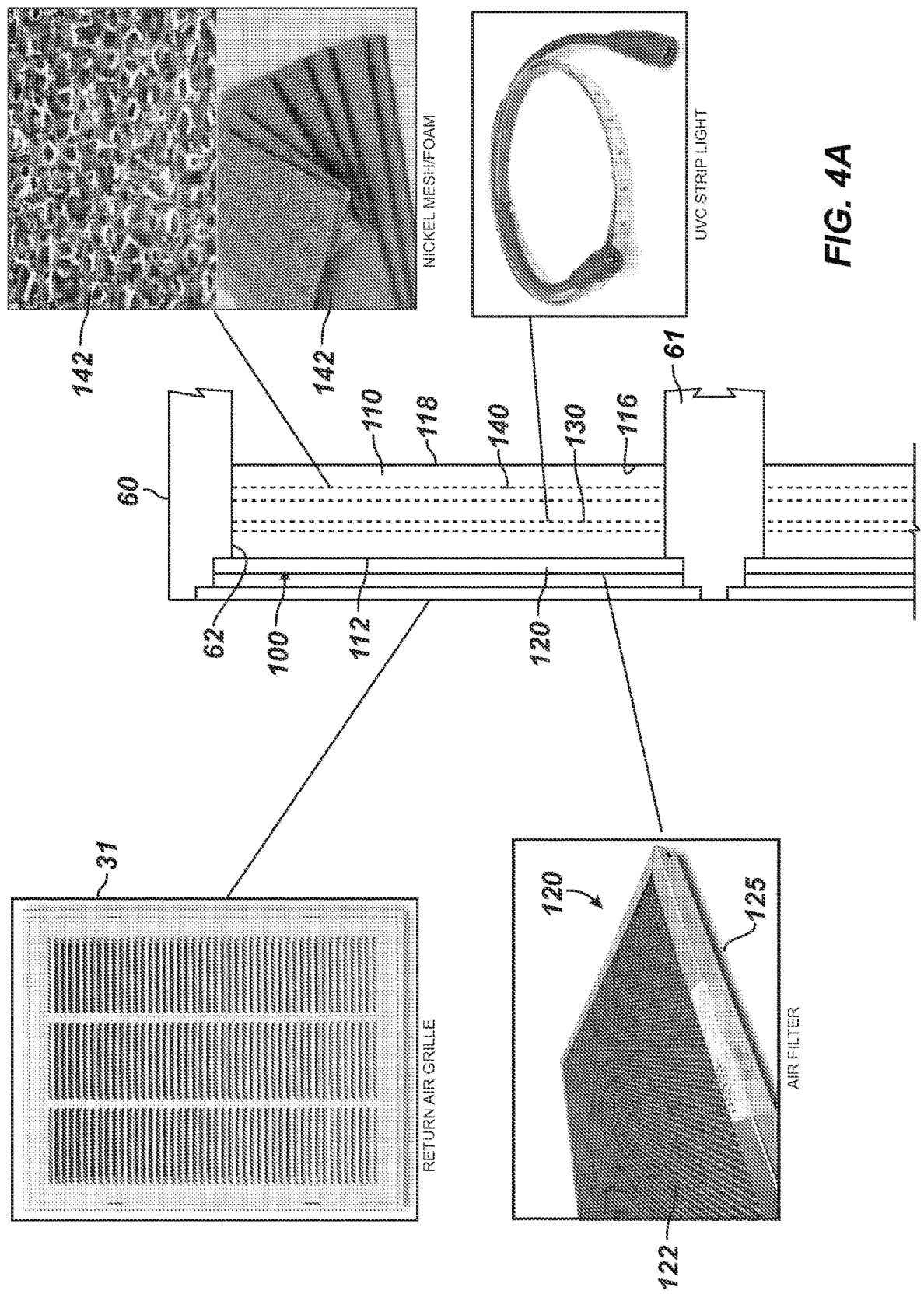
FIGS. 4A and 4B illustrate side schematic views of portion of the disclosed purification device with an arrangement of its components.

Turning to FIG. 4A, a side schematic view of the purification device 50 is shown having an arrangement of its components. As noted previously, the purification cartridge 100 can be used in the intake 62 of the mobile device's housing 60. The frame 110 of the purification cartridge 100 fits in a window, or receptacle of the intake 62 to cover at least a portion the surface area of the opening to the plenum 64. Here, the intake 62 includes a shelf 61 in the housing 60 to support the cartridge 100. The filter 120 can fit into a receptacle of the frame 110, or the filter 120 may abut against the inlet of the frame 110. Typically, the filter 120 simply fits snuggly in the receptacle, but fastening could be used.

The filter 120 for the cartridge 100 can first filter the air flow up to a filtration threshold through the filter 120. In this way, the filter 120 keeps out dust and other particulates from being drawn into cartridge 100 and from being drawing further into the device's housing 60.

As noted herein, an active field of ultraviolet radiation can be produced in the plenum 116 of the cartridge 100 by powering the UV light source 130 disposed in the plenum 116. In the plenum 116 of the cartridge 100, the air flow is impeded up to an impedance threshold through the barrier heater 140 disposed in the plenum 116. The barrier heater 140 includes a permeable barrier 142 (e.g., mesh, foam, screen, tortuous media) of a metal material, such as nickel, nickel alloy, titanium, steel alloy, or other metal material. The permeable barrier 142 can be flat, corrugated, bent, pleated, or the like and can be arranged in one or more layers. The metal mesh/foam 142 of the barrier heater 140 is heated to a surface temperature by supplying a voltage potential across the mesh/foam 142. The UV light source 130 can be disposed in the plenum 116 between the filter 120 and the barrier heater 140 so that the radiation from the source 130 can treat passing air flow and can also treat exposed surfaces of the filter 120 and the barrier heater 140.

Figure 4B:
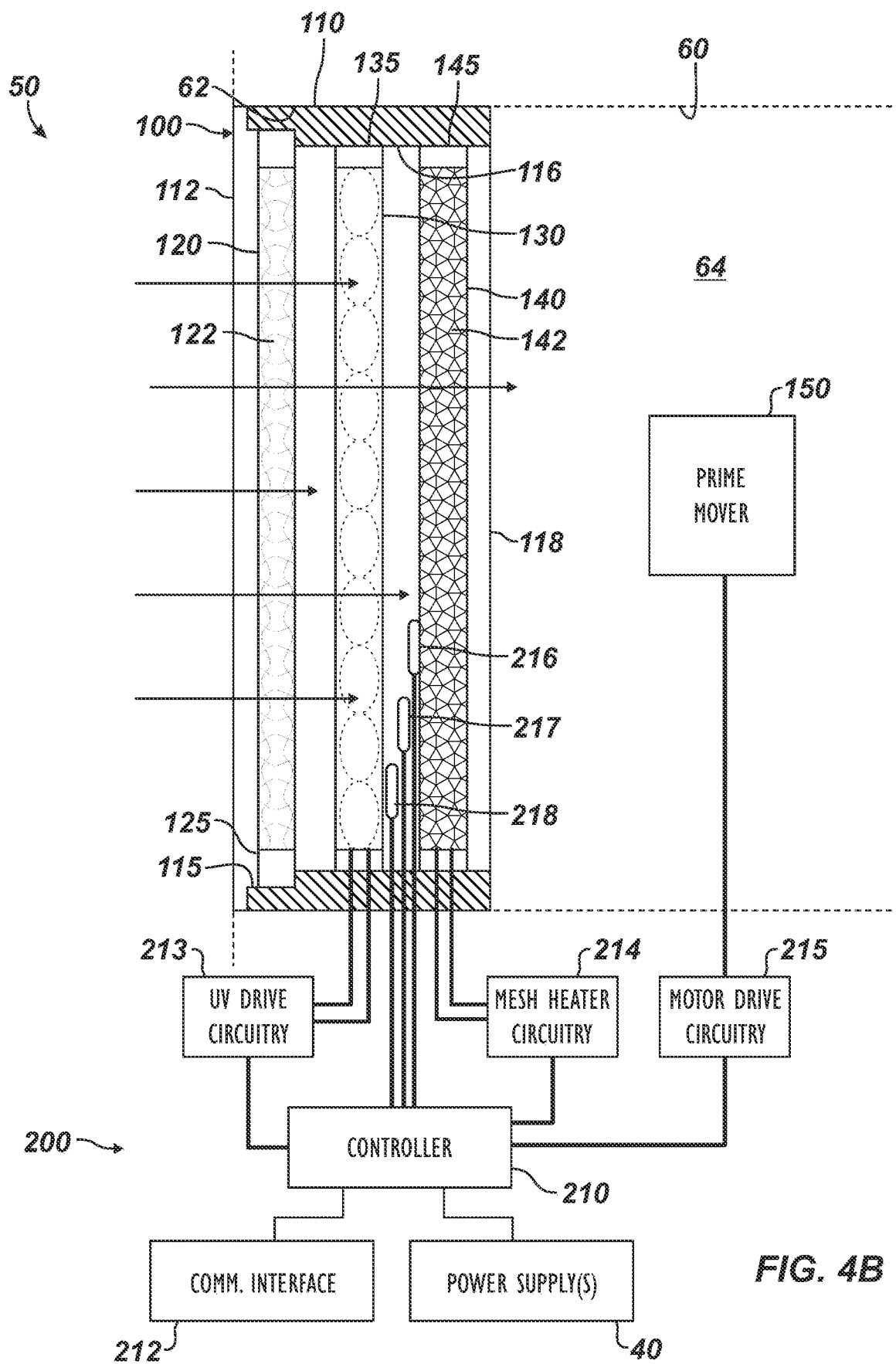
Figure 4C:
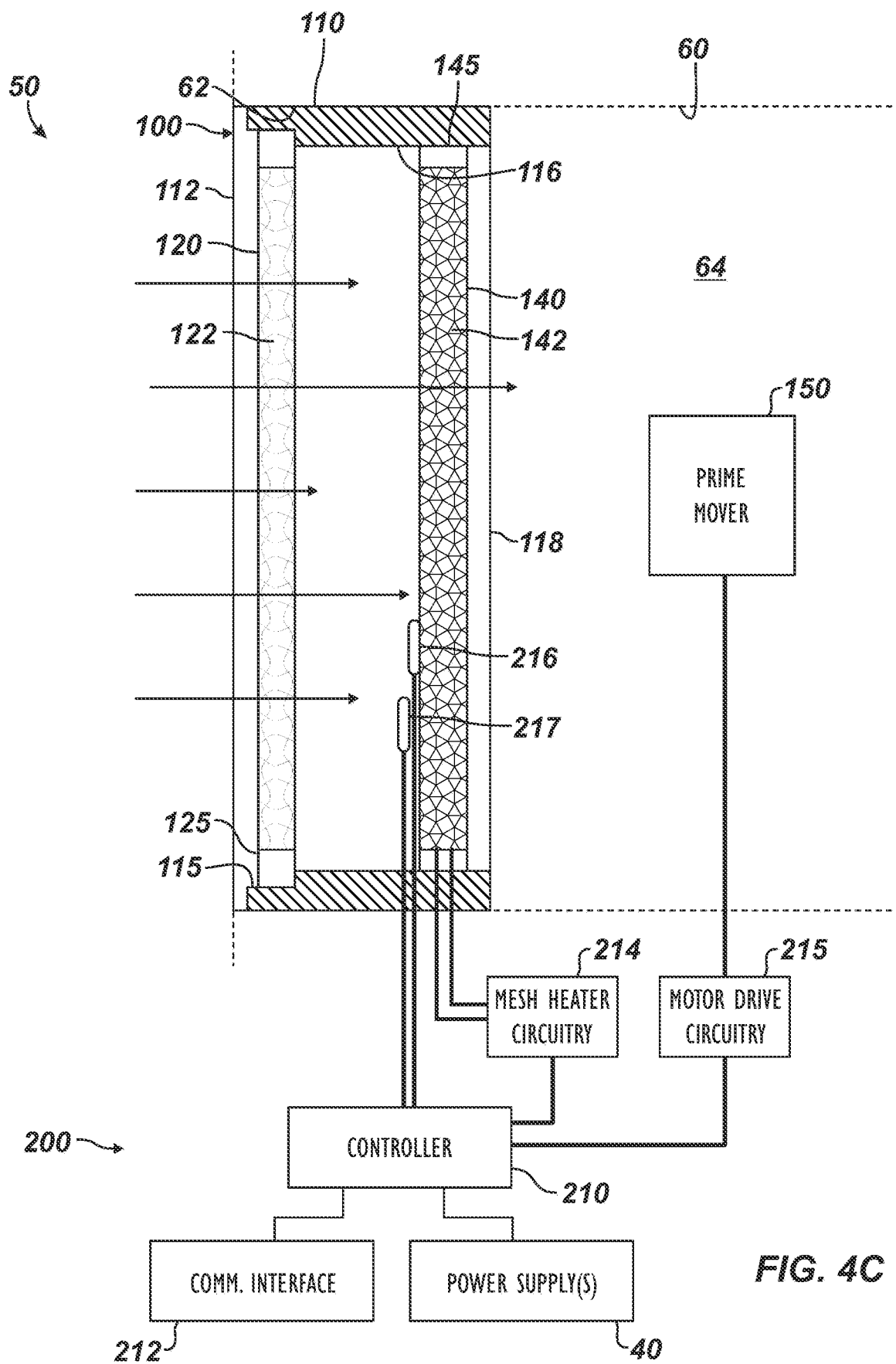
FIG. 4C illustrates a side schematic view of another purification device with an arrangement of its components.
Figure 5A:
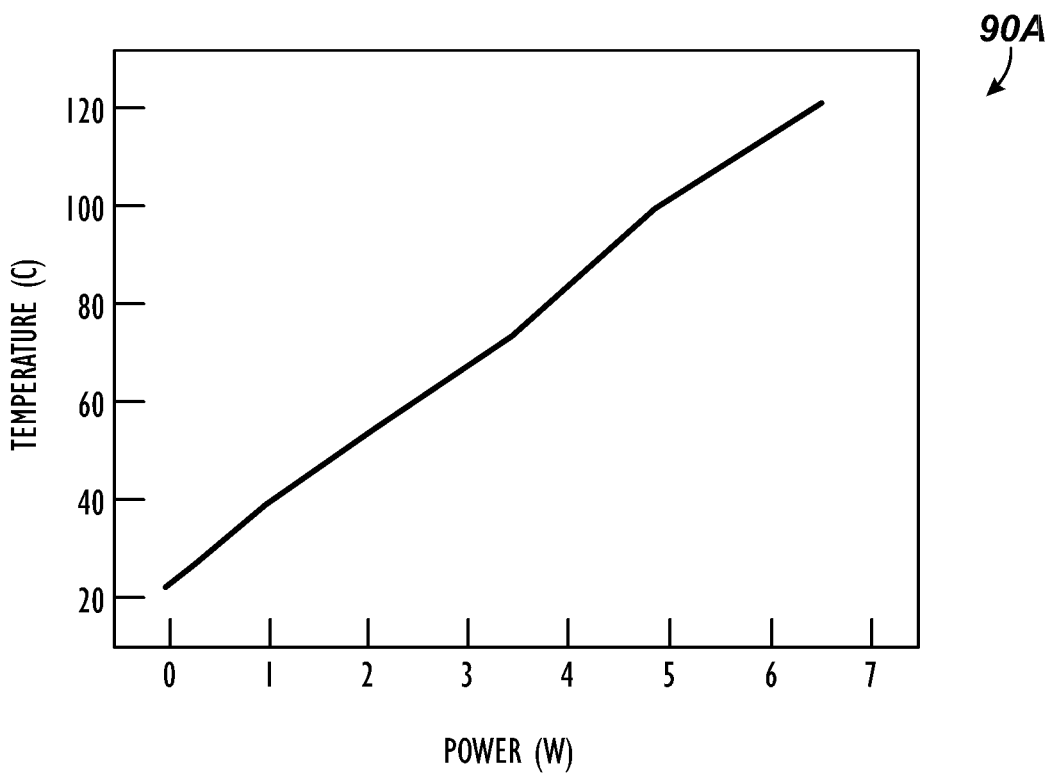
FIGS. 5A, 5B, and 5C illustrate graphs directed to features of a barrier heater for the disclosed purification device.
Figure 5B:
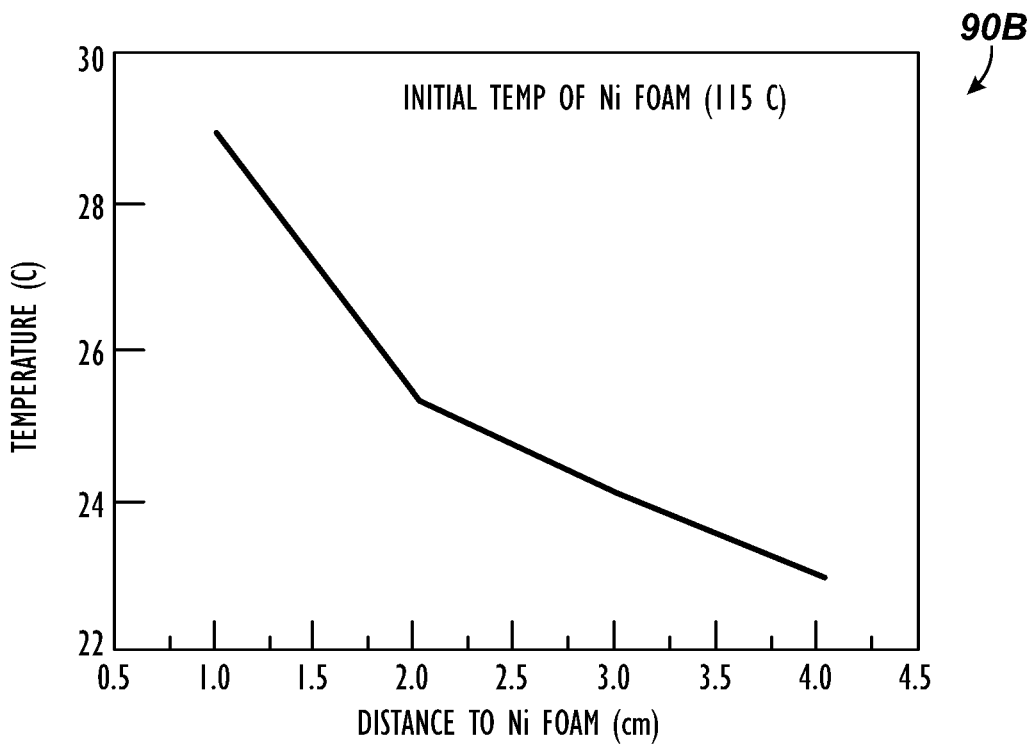
Figure 5C:
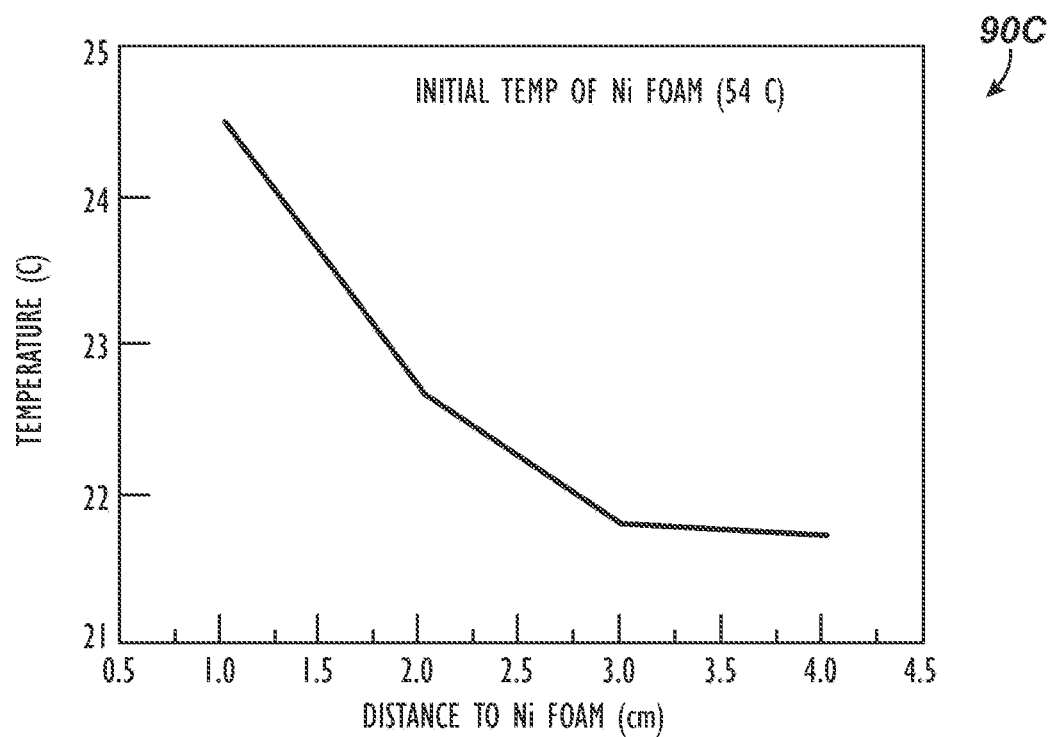

Turning now to FIG. 4B, another side schematic view of a purification device 100 is shown having an arrangement of its components. The frame 110 of a cartridge 100 is shown holding the filter 120, UV light source 130, and barrier heater 140 in its plenum 116, and the cartridge 100 is shown installed in the main plenum 64 of the housing's intake 62. The purification device 50 and cartridge 100 are used with control circuitry and power. For example, the control circuitry includes a controller 200 having appropriate power circuitry and processing circuitry for powering and controlling the purification device 50 and cartridge elements 130, 140. The controller 200 can be connected to one or more types of power supply 40, such as available AC power supplies of a facility, battery power, or other power source. Power circuitry of the controller 200 can convert the supplied power as needed to produce DC power and voltage levels.

Looking at the cartridge 100, the filter 120 is disposed in the plenum 116 of the frame 110 and can be held in a receptacle 115 toward the inlet 112. The filter 120 is composed of a first material and is configured to filter the air flow therethrough up to a filtration threshold. The filter 120 can be a metal filter media 122 composed of stainless steel, aluminum, etc. that is meshed in one or more layers depending on the amount of air flow and the level of filtration required. The filter 120 has a case 125, which is also composed of metal and which frames the metal filter media. In general, the metal filter 120 can be a 1-in thick HVAC filter made from metal that is fire resistant and retardant and that has a high efficiency rating.

The barrier heater 140 is also disposed in the plenum 116 and can be situated toward the outlet 118. Insulation 145 for both heat and electricity may separate the barrier heater 140 from the frame 110. The barrier heater 140 includes a mesh/foam of a metal material and is configured to impede the air flow therethrough up to an impedance threshold.

The UV light source 130 can be disposed in the plenum 116 and, as noted previously, can be situated between the metal filter 120 and barrier heater 140. The UV light source 130 produces an active field of UV-C light in the plenum 116 to treat passing air flow. As noted herein, pathogens, such as viruses, can be eliminated when subjected to a dose of ultraviolet light. For example, the sRNA coronavirus up to 0.11 µm in size can be eliminated >99% with only about 611 µj/cm$^2$ UVGI dose.

Both the UV light source 130 and the barrier heater 140 are connected in electrical communication with the power supply 40 through the controller 200, which controls the illumination of the light source 130 and the heating of the barrier heater 140 in the plenum 116.

The UV light source 130 can include one or more UV-C lamps, a plurality of light emitting diodes, or the like disposed in the plenum 116. For example, the source 130 can use one or more Ultraviolet Germicidal lamps, such as mercury-vapor lamps. The source 130 can also use light emitting diodes having semiconductors to emit UV-C radiation.

One or more structures can be disposed in the frame 110 to support the UV light source 140. The structures used can depend on the type of source 140 used and can include fixtures for lamps and strips for UV-C LEDs. For example, the UV light source 130 can uses several strips of UV-C light emitting diodes stretched across the plenum 116.

The effectiveness of the UVGI treatment in the air flow depends on a number of factors, including the targeted microbial species, the intensity of the exposure, the time of the exposure, and the amount of humidity in the air. A sufficient dose will kill the DNA-based microorganism. Therefore, the intensity of the UVGI treatment, the time for exposure, and other factors can be configured and further controlled in the purification device 100 and HVAC system to reach a desired effectiveness.

The UVGI treatment provided by the purification cartridge 100 can be effective at destroying pathogens, such as COVID-19. The UV-C or short-wave light generated by the UV light source at wavelengths from 100-280 nanometers may have a proven germicidal effect. In particular, 222 nanometer low, far-UVC light is effective at killing and deactivating an aerosolized virus with duration of exposure.

In contrast to conventional use of UVGI in an HVAC system, the disclosed purification device does not require high costs and special installation in air returns or duct systems. Rather, the disclosed cartridge 100 offers practical installation and operation that can be seen as easy as changing an HVAC filter every 1-3 months in your home.

As discussed in more detail below, the metal material of the barrier heater 140 can include nickel mesh/foam. The barrier heater 140 is configured to impede the air flow therethrough up to the impedance threshold of 20 percent, giving the foam a porosity of at least 80%.

The purification cartridge 100 can include anti-microbial coatings on one or more surfaces to eliminate live bacteria and viruses. For example, the filter 120 can have an anti-microbial coating to eliminate pathogens trapped by the filter media. The inside walls of the frame's plenum 116 can also have anti-microbial coating. If practical under heated conditions, the mesh/foam of the barrier heater 140 can have anti-microbial coating.

As further shown in FIG. 4B, the controller 200 of the purification device 50 is disposed in electrical communication with the UV light source 130, the barrier heater 140, and the prime mover 150 and is configured to control (i) the radiation of the UV light source 130 powered by the power supply 40, (ii) the heating of the barrier heater 140 by the power supply 40, and (iii) the air flow generated by the prime mover 150 powered by the power supply 40. This controller 200 is a local controller that can include a communication interface 212 to communicate with other purification devices 50 in a facility environment and other components of an air handing system (20: FIG. 1) in a facility, such as a system controller (25). The local controller 200 can receive a signal from the HVAC system (20), which can indicate the purification device 50 is to be turned on or off. The controller 200 can then the control the illumination, the heating, and the movement of air flow based on the signals received.

To do this, the controller 200 is disposed in electrical communication with heater circuitry 214 connected to the barrier heater 140. At least for a period of time when air is passed through the purification device 50 (being drawn by the prime mover 150), the controller 200 can control the heating of the barrier heater 140 with the heater circuitry 214 powered by the power supply 40. As will be appreciated, the controller 200 and heater circuitry 214 includes any necessary switches, relays, timers, power transformers, etc. to condition and control power supplied to the barrier heater 140.

The controller 200 heats the barrier heater 140 at least when the controller 200 is operating the prime mover 150 to flow air through the device 50. Pre-heating before the prime mover 150 draws return air can occur before air is drawn through the device 50 so that a target temperature can be reached beforehand. This may require an advance signal from the controller 200 or may involve intermittent heating of the barrier heater 140 to maintain some base temperatures Post-heating after the prime mover 150 turns off may also be beneficial for a number of reasons.

The controller 200 is also disposed in electrical communication with drive circuitry 213 connected to the UV light source 130. At least for a period of time when air is being pass through the device 50 (being drawn by the prime mover 150), the controller 200 can control the illumination of the UV light source 130 with the drive circuitry 213 powered by the power supply 40. As will be appreciated, the controller 200 and drive circuitry 213 includes any necessary switches, relays, timers, power transformers, electronic ballast, etc. to condition and control power supplied to the light source 130.

At least when the controller 200 is powering the prime mover 150, the controller 200 illuminates the light source 130. To reach a target illumination, some pre-lighting may be necessary for the lamps or the like of the UV light source 130 to reach full illumination before air is drawn through the device 100. This may require an advance signal from the controller 200. Post-lighting of the source 130 after the prime mover 150 turns off may also be beneficial for a number of reasons.

The controller 200 is also disposed in electrical communication with motor drive circuitry 215 connected to the prime mover 150. To treat the environmental air, the motor drive circuitry 215 operates the prime mover 150, which can then move air through the device 50. As shown, the prime mover 150 may be used to draw air through the device 50 in a manner suitable for filtration arrangements. Of course, other arrangements could be used. The controller 200 may not actuate the prime mover 150 until the UV light source 130 has been brought up to illumination and until the barrier heater 140 has been heated to a target temperature.

For monitoring and control, the controller 200 can include one or more sensors 216, 217, and 218. For example, the controller 200 can include a temperature sensor 216 disposed in the plenum 116 adjacent the barrier heater 140 and disposed in electrical communication with the controller 200. The temperature sensor 216 is configured to measure temperature associated with the heating of the barrier heater 140 so the controller 200 can reach a target temperature. Depending on the implementation and the pathogens to be affected, the barrier heater 140 can heated to the surface temperature over about 54° C. (130° F.). In fact, research shows that heat at about 56° C. or above 56-67° C. (133-152° F.) can kill the SARS coronavirus and that 222-nanometer far-UVC light can be effective at killing and deactivating aerosolized virus.

The controller 200 can be connected to a light sensor 218, such as a photocell or other light sensing element, to monitor the illumination, intensity, wavelength, operation, and the like of the UV light source 130. For example, the UV light source 130 can be configured to produce the ultraviolet radiation with at least 611 μJ/cm2 dose of ultraviolet germicidal irradiation in an active field in the plenum 116, and measurements from the light sensor 218 can monitor the radiation.

The controller 200 can be connected to yet another sensor 217, such as a flow sensor to sense flow, velocity, and the like of the air passing through the plenum 116. The detected flow by the flow sensor 217 may be used by the controller 200 to initiate operation of the UV light source 130 and heater barrier 140 if not signaled already. The velocity of the flow may be measured by the flow sensor 217 to coordinate a target flow velocity through the device 100 so the heating of the air flow by the barrier heater 140 can be coordinated to the detected flow velocity and a target heating level. The velocity of the flow may also be monitored to coordinate the target irradiation of the irradiation of the air flow by the UV light source 140 so appropriate exposure levels can be achieved.

The flow sensor 217 can monitor the flow and velocity of the air passing through the device 50. In turn, this sensed information can be used as feedback by the controller 200 to adjust the operation of the prime mover 150. In this way, the controller 150 can adjust the flow and velocity to a level best suited to treat the air passing through the plenum 116 to be exposed to the UV illumination of the UV light source 130 and the heat of the barrier heater 140. A target velocity of the air flow can be reached that best suites the target illumination and temperature to treat the air effectively depending on the implementation or environmental circumstances.

As noted herein, the purification device 50 combines thermal energy with UV-C light and is constructed within a flame retardant and resistant filtration system. The device 50 can be placed in an environment. As disclosed herein, embodiments of the purification device 100 include the barrier heater 140 and can thereby include the various features of the controller 200, sensors, etc. discussed above for the barrier heater 140. Some embodiments may not include the UV light source 130, while other embodiments may include the UV light source 130 along with the various features of the controller 200, sensors, etc. discussed above for the UV light source 130. In particular, FIG. 4C illustrates another side schematic view of a purification device 100 having an arrangement of its components without a UV light source. Similar components are provided the same reference numerals as other embodiments and are not repeated here.

As proposed, the disclosed purification device 50 can eliminate pathogens, such as COVID-19, while filtering the air to 99.97% (ASME, U.S. DOE) of particles. As disclosed in the co-pending application incorporated herein, the configuration can be integrated into an air handling system (20) of a facility.

Although the purification cartridge 50 has been described above as including a frame 110 that accommodates an air filter in the frame 110. The cartridge 50 can include a frame 110 that mounts in the housing 60 already accommodating a filter. In this types of arrangement, the purification cartridge 100 can include a frame 110, an UV light source 130, and a barrier heater 140 as before, but the frame 110 does not necessarily hold or receive an air filter 120. Instead, a separate air filter can be installed at the intake 62 of the housing 60.

Discussion now turns to details of the barrier heater 140 of the disclosed purification device 100. The metal mesh/foam of the barrier heater 140 can have one or more layers of material and can have a suitable thickness. As one example, the mesh/foam may have thickness of 0.5 mm to 2.0 mm. Composed of nickel (Ni), mesh/foam may have surface charge density (o) of $1.43\times10^7$ C/$m^2$. The Ni mesh/foam is electrically conductive, and it is highly-porous having random three-dimensional channels defined there-through. The mesh/foam exhibits resistance of about 00.178Ω, and the electrical resistivity of an exemplary Ni foam is calculated to be about $1.51\times10^{-5}$ Ωm.

For example, FIG. 5A illustrates a first graph 90A of the temperature (C) produced by an exemplary Ni foam material for the barrier heater per unit of supplied power (W). A sample of the foam having a size of 1.65 mm×195 mm×10 mm was investigated. The temperature was measured after applying voltage for a time period until the temperature became stable. As shown in the graph 90A, the temperature is shown to rise generally linearly per unit supplied power so that about 7 watts produces a temperature of about 120° C. (248° F.).

FIG. 5B illustrates a second graph 90B of the measured temperature of gas (e.g., $N_2$) after flowing through the exemplary Ni foam material for the barrier heater heated to a temperature. The gas for the measurement was originated from an upstream distance of about 3.5 cm from the heated Ni foam material while room temperatures was about 21.7° C. (71° F.). Temperature measurements were made at different downstream distances relative to the exemplary Ni foam material, which was heated to an initial temperature of about 115° C. (239° F.). As can be seen, the measured temperature of the gas decreased from about 29° C. to 23° C. (84° F. to 73° F.) for downstream distances ranging from 1 cm to 4 cm from the exemplary Ni foam material. This indicates that the heating produced by the barrier heater 140 composed of such an exemplary Ni foam material provides a tortuous heated surface area against which the air flow and any pathogens can impact, but the heating is localized and dissipated in the downstream air flow.

FIG. 5C illustrates another graph 90C of the measured temperature made at different downstream distances relative to the exemplary Ni foam material at another initial temperature. Here, the Ni foam material is at an initial temperatures of about 54° C. (129° F.). The measured temperature of the gas decreased from about 24.5° C. to 21.7° C. (76° F. to 71° F.) for distances ranging from 1 cm to 4 cm from the exemplary Ni foam material.

As noted herein, the barrier heater 140 can use nickel, nickel-based alloys, or iron-based alloys developed for applications at high service temperatures and in corrosive environments. Nickel is slowly oxidized by air at room temperature and is considered corrosion-resistant. Nickel is a high performance metal that can be easily regulated to reach high temperatures with minimal transmission of heat to its surroundings or to air molecules passing through it. When voltage is passed through nickel mesh/foam (1.43× $10^7 \sigma$), for example, the metal conducts energy to a target temperature hot enough to kill pathogens, including COVID-19 on contact. The target temperature can be (56° C. to 66° C. or more, and even over 93° C.) (133° F. to 150° F. or more, and even over 200° F. In this way, the Ni mesh/foam (0.5 mm-2.0 mm) provides a heated, charged surface area for the pathogen to impact and be eliminated by the heated latticework. Meanwhile, the porosity (80-90%) of the foam/mesh of the barrier heater 140 does not impede air flow and does not detrimentally increase the energy required from the purification device 50 to operate the prime mover 150.

As disclosed above, heating in the plenum 116 can be achieved with a barrier heater 140 having the mesh/foam that is heated to the target temperature and provides a tortuous path for return air passing through the mesh/foam. Other forms of heating can be used. As disclosed above, UV illumination in the plenum 116 can be achieved with UV light strips. Other forms of UV illumination can be used.

Figure 6A:
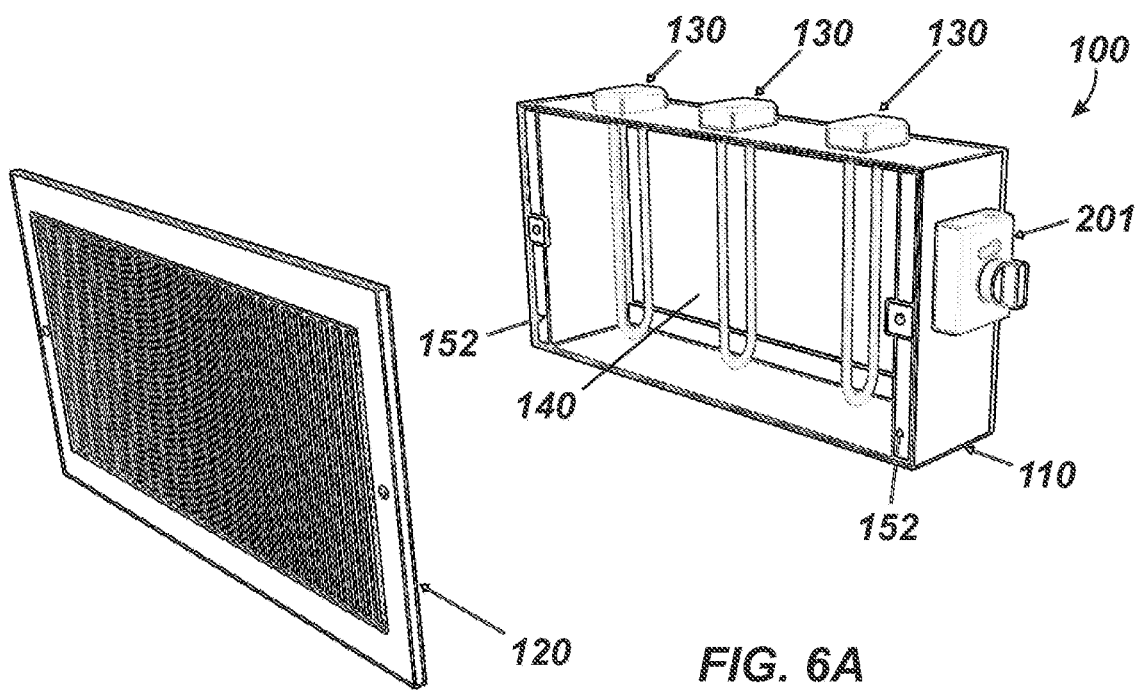
FIG. 6A illustrates another heating arrangement having a plurality of electric elements disposed in a plenum of a frame and connected to a power source control.

For example, FIG. 6A shows another arrangement for a purification cartridge 100 having a plurality of electric elements (UV light sources 130 and a barrier heater 140) disposed in a plenum 116 of a frame 110 and connected to a power source control 201. The plenum 116 includes carbon media 152 on one or more sidewalls for absorption and purification purposes. The plenum 116 may also include a filter 120 that is disposed at the inlet.

Figure 6D:
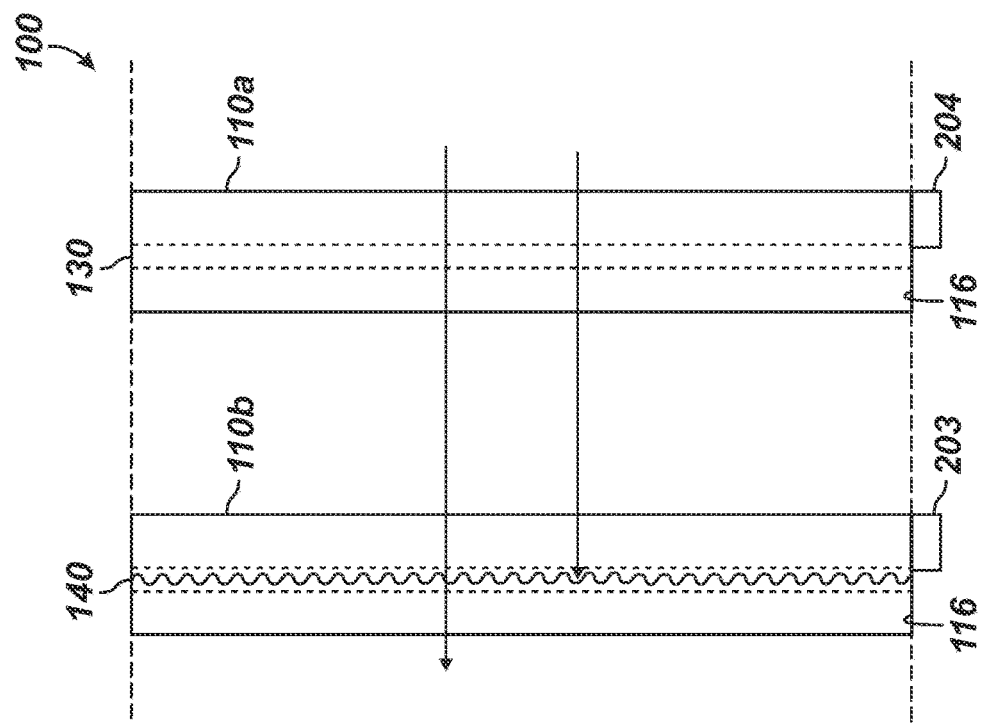
FIGS. 6B, 6C, and 6D illustrate other configurations for cartridges of the disclosed purification device.

As hinted to above, the disclosed purification cartridge 100 can be used separately or in combination with other purification cartridges 100. As one example, FIG. 6B shows a configuration of a purification cartridge 100 according to the present disclosure, which includes a UV light source 130 and a barrier heater 140 controlled by control/power circuitry 202. The UV light source 130 and the barrier heater 140 can be similar to those disclosed herein and can be housed together in a housing or frame 110 to fit into the air flow of the device's housing (60). For example, the housing or frame 110 can fit into the device's housing (60) through the inlet or elsewhere. Filtering can be achieved elsewhere in the housing (60). For its part, the control/power circuitry 201 may have the necessary components as disclosed herein to control the UV light source 130 and the barrier heater 140.

Figure 6C:
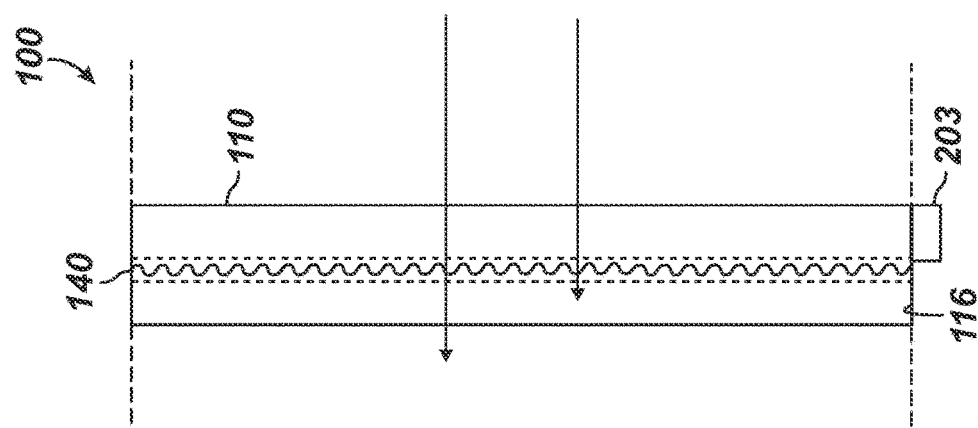
Figure 6B:
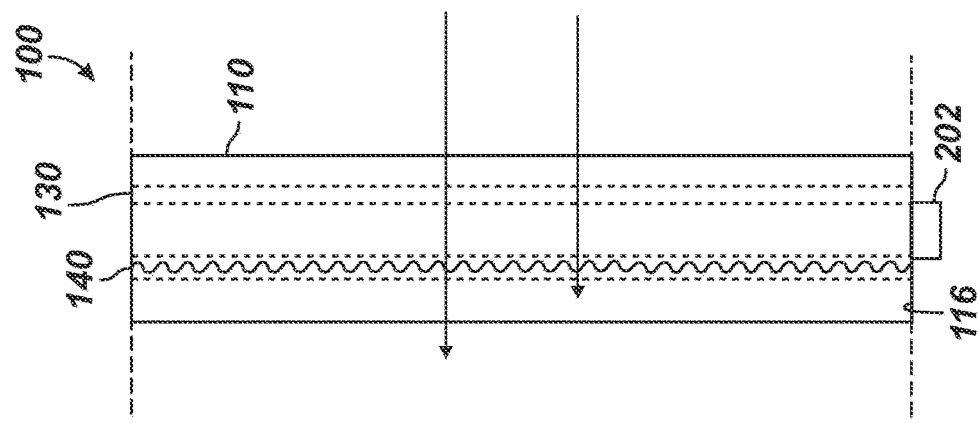

As another example, FIG. 6C shows another configuration of a purification cartridge 100 according to the present disclosure, which includes a barrier heater 140 controlled by control/power circuitry 203. This device 100 as shown may not include a UV light source, although such a source could be used elsewhere in a facility or other environment. The barrier heater 140 can be similar to those disclosed herein and can be housed in a housing or frame 110 to fit into the device's housing (60). For example, the housing or frame 110 can fit into the intake of the device's housing (60) or can fit elsewhere in the air flow. Filtering can be achieved elsewhere or can be incorporated into the frame 110 using a filter (not shown) as disclosed elsewhere herein. For its part, the control/power circuitry 203 may have the necessary components as disclosed herein to control the barrier heater 140.

As yet another example, FIG. 6D shows yet another configuration of purification cartridges 100a-b according to the present disclosure, which includes a UV light source 130 controlled by control/power circuitry 204 and includes a barrier heater 140 controlled by control/power circuitry 203. The UV light source 130 and the barrier heater 140 can be similar to those disclosed herein and can be housed in separate housings or frames 110a-b to fit into the device's housing (60). For example, the frames 110a-b can fit into the intake of the housing (60) or can be configured elsewhere. Filtering can be achieved elsewhere or can be incorporated into either one or both of the frames 110a-b using a filter (not shown) as disclosed elsewhere herein. For their parts, the control/power circuitry 203, 204 may have the necessary components as disclosed herein to control the UV light source 130 and the barrier heater 140 respectively.

Figure 7A:
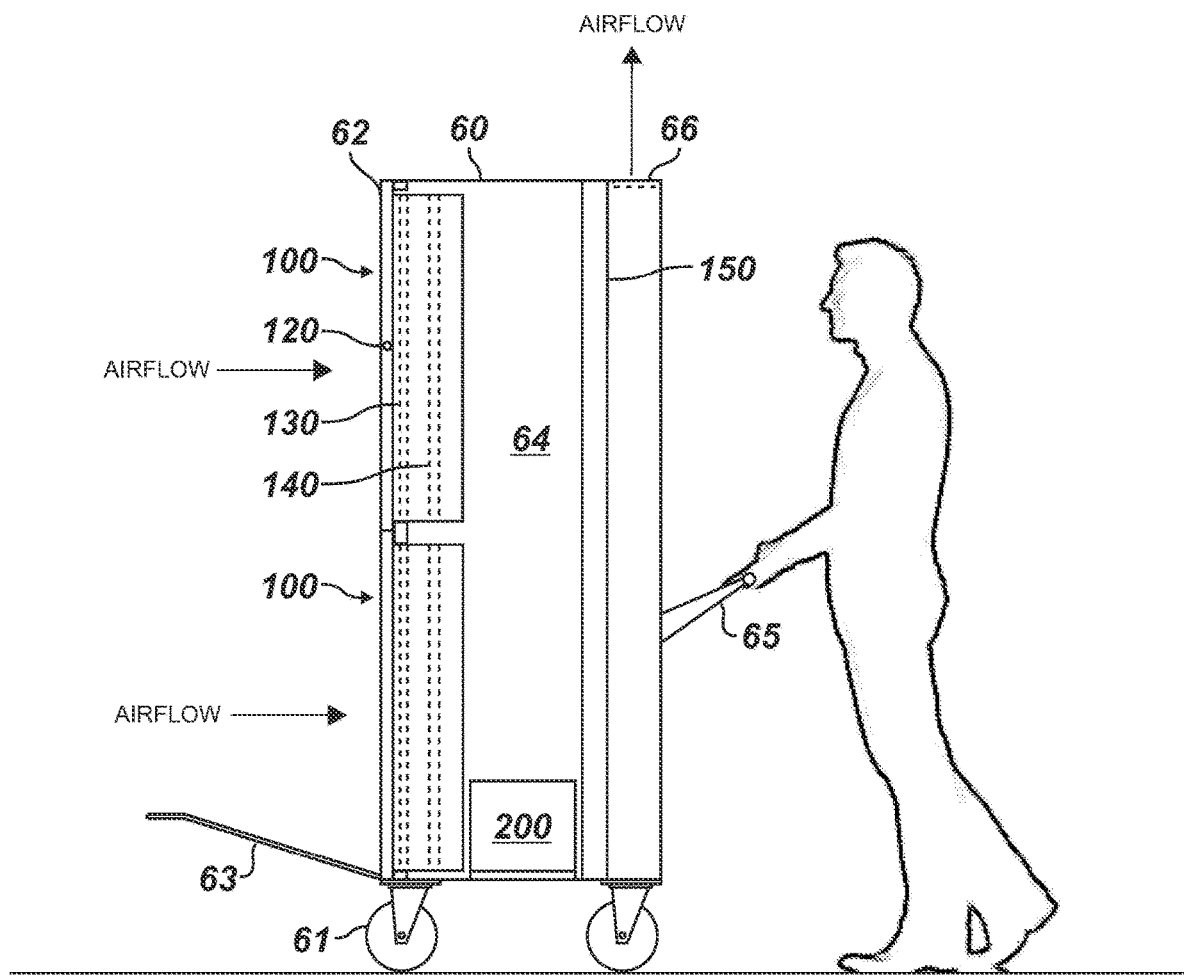
FIG. 7A shows how the mobile purification device can be moved in a facility environment.

FIG. 7A shows how a purification device 50 can be moved around in a facility environment. The caster wheels 61, tow hitch 63, and handle 65 allow the device 50 to be placed as desired. Although configured for a particular implementation, a typical size for the housing 60 may include overall dimensions of 20 to 40-in width×60-in height×24-in depth. When cartridges 100 are used, the dimensions of the cartridges 100 can be suited to the overall dimension of the housing 60. A typical size for the cartridge 100 may include overall dimensions of 20 to 40-in width×30 to 60-in height×7 to 14-in depth. These values are only given for example implementations.

Figure 7B:
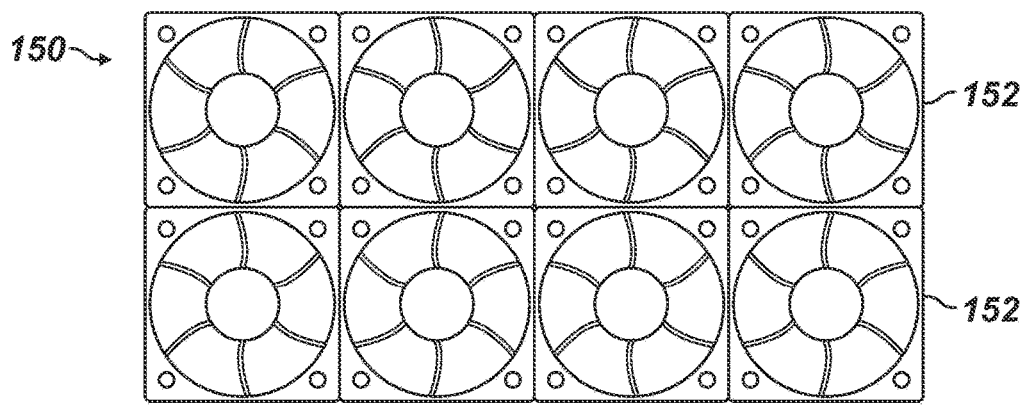
FIG. 7B illustrates a plurality of electric fans arranged for a prime mover for the disclosure purification device.

As noted above, the prime mover 150 in the purification device 50 for moving the air in the housing 60 can use one or more blowers or fans. FIG. 7B shows an example of a set of fans 152 that can be arranged in the housing (60) to move air. Six fans 152 are shown here just as an example. More or fewer fans can be used to cover the surface area across the housing (60), depending on the size of each fan 152. Multiple fans 152 can be used across the surface area to draw air consistently through the intake (62) of the housing (60). Suitable fans 152 for such an arrangement can include electric fans having variable speed control, such as commonly used as cooling fans for cabinet installations, audio visual enclosures, etc.

Figure 8:
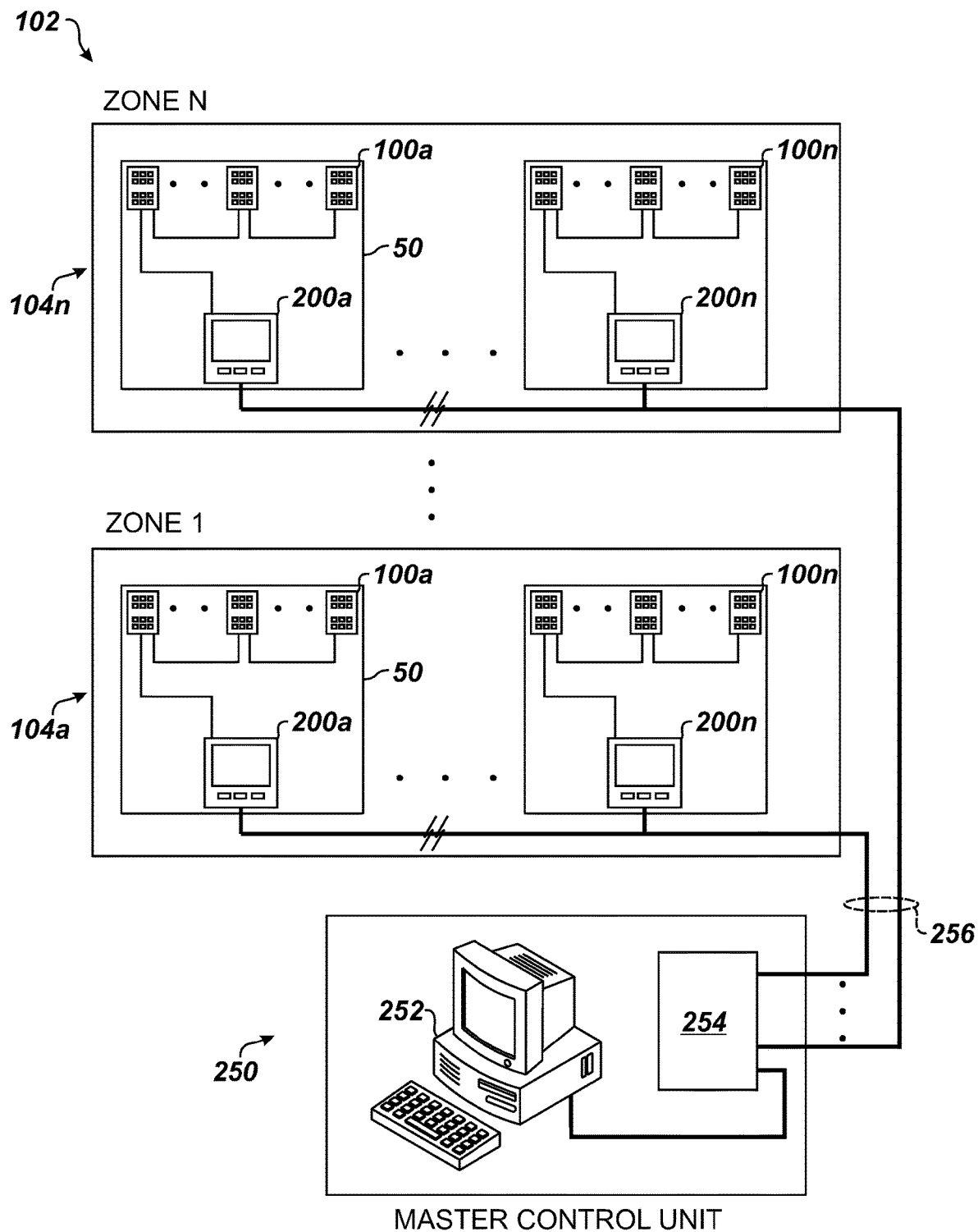
FIG. 8 illustrates a configuration having a number of purification devices subject to a master control unit.

As noted above, more than one purification device 50 can be used in a facility environment, and these devices 50 can have control configurations for remote or localized control. For example, FIG. 8 shows a number of different mobile purification devices 50 situated about various zones of a facility environment. A master control unit 250 has a central processing unit 252 and used communication interfaces 245 for communicating via wired and/or wireless communications 256 with multiple local controllers 200a-n in the different zones 104a-n of a facility environment 102. Each of the local controllers 200a-n can control the one or more of the purification cartridges 100a-n in the device 50.

As noted previously, the permeable barrier 142 of the barrier heater 140 disclosed herein can have different layers and configurations. In FIG. 9A, a portion of a barrier heater 140a is shown with the permeable barrier 142 being flat and having a defined thickness T1. One or more such flat barriers 142 can be used adjacent one another in series to impede and interact with the impinging air flow. To increase surface area and the interaction, a portion of a barrier heater 140b is shown in FIG. 9B having folds, corrugations, or pleats 142 in the permeable barrier 142. The mesh material of the barrier 142 may have its original thickness T1, but the corrugated barrier heater 140b presents a thickness of T2 for the impinging air flow. One or more such corrugated barriers 142 can be used adjacent one another in series to impede and interact with the impinging air flow.

Considering the flexibility of Ni foam, the corrugated barrier heater 140b offers several advantages. First, the resistance of the Ni foam is much larger with the bends 144, which can help the barrier heater 140b when used with the residential voltage (110 V). Second, as illustrated in FIG.

9B, the bends 144 produce an effective distance T2 multiple times greater than the thickness T1 for interacting with the impinging air. The gaps between the bends 144 in the hot Ni foam create a high temperature that can be effective in damaging pathogens. It should be noted that the number of bends, the bending length, and the like can be easily controlled, and the longer the bending length, the higher the temperature can be achieved. Third, compared to the flat Ni foam with two main sides exposing to air, the bended Ni foam barrier 140b in FIG. 9B has a much smaller area exposed to the incoming and outgoing air, which will minimize the heat loss, so temperature of the barrier heater 140 can increase more rapidly and can reach to a much higher value at the same power consumption.

For example, FIG. 10A illustrates a graph of input voltage relative to the current produced for the barrier heater 140a having a flat Ni foam configuration, and FIG. 10B illustrates another graph of the current relative to a temperature level produced for the barrier heater 140a having the flat Ni foam configuration. Meanwhile, FIG. 11A illustrates a graph of input voltage relative to the current produced for the barrier heater 140b having corrugated Ni foam configuration, and FIG. 11B illustrates another graph of the current relative to a temperature level produced for the barrier heater 140b having the corrugated Ni foam configuration. As can be seen in FIGS. 10B and 11B, under the same voltage of 1.0 V, the temperature of the corrugated barrier heater 140b can be more than twice that of the flat barrier heater 140a.

As will be appreciated, various features of the disclosed purification device 100 with its UV light source 130 and barrier heater 140 can be configured to meet a particular implementation and to treat air for particular pathogens. Testing with actual pathogens requires careful controls, which has been conducted in laboratory environments.

As to the UV light source 130, the intensity, the active area, the wavelength, and other variables of the UV light from the source 130 can be configured to treat air for particular pathogens, and the variables are best determined by direct testing with actual pathogens in a controlled laboratory setting.

As to the barrier heater 140, the thickness, material, active surface area, permeability, corrugations, temperature, and other variables of the permeable barrier 142 from the barrier heater 140 can be configured to treat air for particular pathogens, and the variables are best determined by direct testing with actual pathogens in a controlled laboratory setting.

Previous studies with SARS-COV and MERS-COV have established that coronaviruses can be inactivated by heat. See e.g., Leclerca, 2014; Darnell, 2004; Pastorino, 2020. Results of a preliminary study in a BSL3 facility showed SARS-COV-2 is remarkably heat-resistant for an enveloped RNA virus. Only the 100° C. for 10 minutes protocol totally inactivated the virus.

Figure 12:
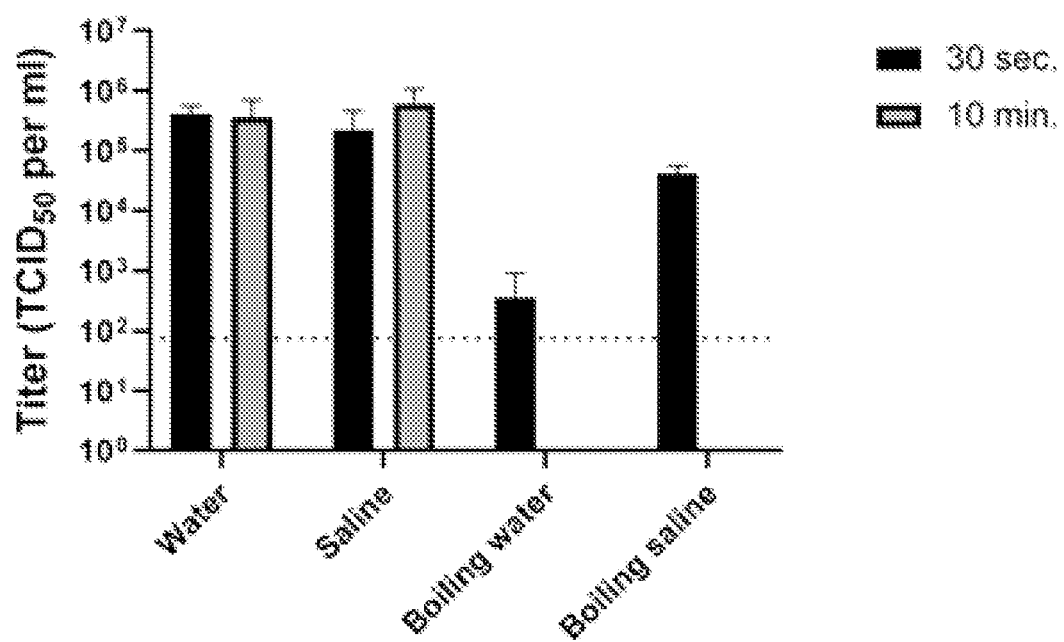
FIG. 12 illustrates a graph of exposure times and temperatures.

In particular, heat resistance of the Human SARS-COV-2 strain (COVID-19) has been conducted in a BSL3 facility. The protocols for the study included using water and saline either at room temperature or at boiling temperature (FIG. 12). For the latter, 10 μL of SARS-COV-2 was added to 90 μL of preheated water or saline at 100° C. (212° F.). These solutions were either incubated at 100° C. for either 30 seconds or 10 minutes whereas for the control arm incubation was carried out at room temperature.

After the incubation, 900 μL room-temperature media was added and titrated. The control arm of 10 min and 30 seconds incubation at room temperature remained ineffective in reducing the virus load. By contrast, the protocol 100° C.-30 seconds depicted a trend, but the exposure apparently was not long enough to effectively reduce the virus load, although the virus load in water was relatively lower compared to saline. Only the 100° C.-10 minute protocol for either water or saline was able to totally inactivate the virus (>5 $Log_{10}$ decrease).

The generated data confirms the virus to be remarkably heat-resistant for an enveloped RNA virus. Additional studies about the heat inactivation can illustrate curves for variable temperatures (50° C., 100° C., 150° C., 200° C., 250° C. & 300° C.) and exposure durations (1 sec, 5 sec, 15 sec, 30 sec, 1 min, 3 min, & 5 min), which can then be correlated to the expected heat damage caused by a barrier heater as disclosed herein, such as having a permeable Ni foam.

According to recent research, however, the heated filter of the disclosed barrier heater 140 can be used safely at high temperatures [(200-250° C.) (392-482° F.)] to kill COVID-19. In particular, research has been conducted at the Galveston National Lab/NIAID Biodefense Laboratory Network (Biosafety Level 4) and include findings of controlled experiments. The research has found COVID-19 to be vaporized in aerosolized air on contact with the specialized heated filter system of the present disclosure (i.e., the disclosed barrier heater 140). The results show a 100-fold decrease in active virus and a 100-percent kill rate of COVID-19 by the heated barrier heater 140. This research shows how COVID-19 can be eliminated from the air.

The disclosed purification device 100 can kill viruses and bacteria in the cycling air efficiently at high temperatures (250° C.) (482° F.). As disclosed herein, the barrier heater 140, such as the nickel (Ni) foam, is low cost, electrically conductive, highly porous with random channels, and mechanically strong with good flexibility, which act as a good filter for sterilization and disinfection in an HVAC system or other environment. A bended Ni foam provides a structure with higher resistance and lower voltage and increases surface area for sterilization. A mechanical kill using temperature and a supercharged, high performance metal may be applied to the setting of COVID-19.

Other related research as disclosed herein has found that there is not a significant temperature increase in the air that passes through the disclosed heated filter given its high performance and design. Primary research of the filter and is conductivity was completed at the Superconductivity Center of Texas at The University of Houston. Research partners include Texas A&M University, Department of Engineering and Engineering Experiment Station and the University of Texas Medical Branch. As has been illustrated, the temperature of the barrier heater 140 of Ni foam increases very fast and can be heated to a high temperature with low wattage power. The air temperature decreases very fast after passing through the heated Ni foam of the barrier heater 140, even at temperatures over 100° C. (212° F.), the air temperature is room temperature at 4 cm away.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. An apparatus used with supplied power for treating air in an environment for a pathogen, the apparatus comprising:
   a housing being mobile in the environment and having an intake and an exhaust;
   at least one prime mover disposed in the housing between the intake and the exhaust and being operable to move the air in the environment through the housing from the intake to the exhaust;
   at least one heater disposed in the housing and comprising a permeable barrier having a metal material, the permeable barrier being configured to allow the moved air flow therethrough up to a porosity threshold, the metal material of the permeable barrier being connected in electrical communication to the supplied power, and the permeable barrier having an active surface area being configured to interact with the pathogen and being heated by the supplied power to a surface temperature directed to at least damage the pathogen; and
   a controller in electrical communication with the permeable barrier of the at least one heater via heater circuitry to control the heating of the permeable barrier by the supplied power and in electrical communication with the at least one prime mover via drive circuitry to control the air flow through the housing from the intake to the exhaust generated by the at least one prime mover powered by the supplied power.

2. The apparatus of claim 1, further comprising at least one filter disposed in the housing and comprising a first material, the filter configured to filter the moved air therethrough up to a filtration threshold.

3. The apparatus of claim 1, wherein the first material of the filter comprises a metal material.

4. The apparatus of claim 1, further comprising at least one cartridge being replaceable at the intake of the housing, the at least one cartridge having a plenum with an inlet and an outlet, the at least one cartridge having the at least one permeable barrier.

5. The apparatus of claim 4, wherein the at least one cartridge further comprises at least one filter disposed across the plenum and comprising a first material, the filter being configured to filter the moved air therethrough up to a filtration threshold.

6. The apparatus of claim 1, further comprising at least one ultraviolet light source disposed in the housing, the ultraviolet light source connected in electrical communication with the supplied power and being configured to generate an active field of ultraviolet radiation in at least one a portion of the housing through which the moved air passes from the intake to the exhaust.

7. The apparatus of claim 6, wherein the apparatus further comprises at least one cartridge being replaceable at the intake of the housing, the at least one cartridge having a plenum with an inlet and an outlet, the at least one cartridge having the at least one ultraviolet light source and the permeable barrier.

8. The apparatus of claim 6, wherein the ultraviolet light source comprises one or more UV-C lamps or a plurality of UV-C light emitting diodes disposed in the plenum.

9. The apparatus of claim 4, wherein the at least one cartridge comprises a plurality of sidewalls enclosing the plenum between an open side for the inlet and an opposing open side for the outlet.

10. The apparatus of claim 9, further comprising electrical insulation disposed between an edge of the permeable barrier and the sidewalls of the at least one cartridge.

11. The apparatus of claim 1, wherein the prime mover comprises one or more blowers or fans.

12. The apparatus of claim 1, wherein the apparatus comprises a power supply disposed on the housing and supplying the supplied power.

13. The apparatus of claim 1, wherein the permeable barrier of the at least one heater comprises a mesh, a foam, a screen, or a tortuous media.

14. The apparatus of claim 1, wherein the metal material of the permeable barrier comprises nickel, nickel-based alloy, iron-based alloy, titanium, or steel alloy.

15. The apparatus of claim 1, wherein to allow the air flow up to the porosity threshold, the permeable barrier of the at least one heater is configured to impede the air flow therethrough up to an impedance threshold of about 20 percent, giving the permeable barrier the porosity threshold of at least about 80 percent.

16. The apparatus of claim 1, wherein the permeable barrier of the at least one heater is heated to the surface temperature of at least greater than about 56° C. (133° F.).

17. The apparatus of claim 1, further comprising a temperature sensor disposed adjacent the permeable barrier and disposed in electrical communication with the controller, the temperature sensor being configured to measure a temperature associated with the heating of the permeable barrier.

18. The apparatus of claim 1, further comprising an ultraviolet light source disposed in the housing, the ultraviolet light source connected in electrical communication with the supplied power and being configured to generate an active field of ultraviolet radiation in at least one a portion of the housing through which the moved air passes from the intake to the exhaust, wherein the controller is disposed in electrical communication with drive circuitry connected to the ultraviolet light source, the controller configured to control the ultraviolet radiation of the ultraviolet light source with the drive circuitry powered by the supplied power.

19. The apparatus of claim 18, further comprising a light sensor disposed adjacent the ultraviolet light source and disposed in electrical communication with the controller, the light sensor being configured to measure the ultraviolet radiation associated with the ultraviolet light source.

20. The apparatus of claim 1, further comprising a flow sensor disposed in the housing and disposed in electrical communication with the controller, the flow sensor being configured to measure the air flow passing through the housing, the controller configuring the control based on the measured air flow.

* * * * *